United States Patent [19]

Bouchard et al.

[11] Patent Number: 5,840,931

[45] Date of Patent: Nov. 24, 1998

[54] TAXOIDS, THEIR PREPARATION AND PHARMACEUTICAL COMPOSITIONS CONTAINING THEM

[75] Inventors: Hervé Bouchard, Thiais; Jean-Dominique Bourzat, Vincennes; Alain Commerçon, Vitry-sur-Seine; Corinne Terrier, Livry-Gargan; Martine Zucco, Thiais, all of France

[73] Assignee: Rhone-Poulenc Rorer S.A., Antony, France

[21] Appl. No.: 817,742

[22] PCT Filed: Oct. 23, 1995

[86] PCT No.: PCT/FR95/01393

§ 371 Date: Apr. 24, 1997

§ 102(e) Date: Apr. 24, 1997

[87] PCT Pub. No.: WO96/13494

PCT Pub. Date: May 9, 1996

[30]   Foreign Application Priority Data

Oct. 26, 1994 [FR]   France ................................. 94 12795

[51] Int. Cl.$^6$ ................................................. C07D 305/14
[52] U.S. Cl. ............................................ 549/510; 549/511
[58] Field of Search ...................... 549/510, 511; 514/449

[56]   References Cited

U.S. PATENT DOCUMENTS 5,254,580  10/1993  Chen et al. .............................. 514/449
5,399,726  3/1995  Holton et al. ........................... 549/510

FOREIGN PATENT DOCUMENTS

WO 94/13654  6/1994  WIPO .
WO 94/13655  6/1994  WIPO .
WO 95/09163  4/1995  WIPO .

Primary Examiner—Ba K. Trinh

Attorney, Agent, or Firm—Finnegan, Henderson, Farabow, Garrett & Dunner, L.L.P.

[57]   ABSTRACT

This invention relates to compounds of the formula (I), preparation thereof, and pharmaceutical compositions containing them:

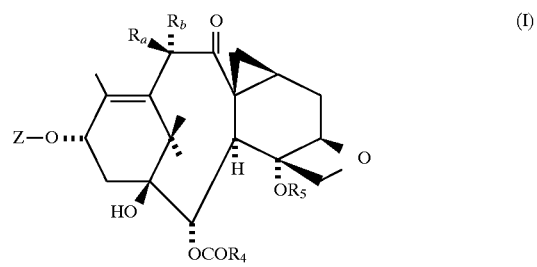

wherein: $R_a$ is hydrogen, hydroxyl, alkoxy, acyloxy, or an alkoxyacetoxy radical; $R_b$ is hydrogen; or $R_a$ and $R_b$, together with the carbon atom to which they are attached, form a ketone function; Z represents a hydrogen atom or a radical of formula (II):

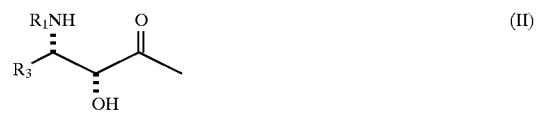

in which: $R_1$ represents an optionally substituted benzoyl, thenoyl, furoyl, or $R_2$—O—CO— radical where $R_2$ is an alkyl, alkenyl, alkynyl, cycloalkyl, cycloalkenyl, bicycloalkyl, or an optionally substituted phenyl or heterocyclic radical; $R_3$ is an aromatic heterocyclic, alkyl, alkenyl, alkynyl, cycloalkyl, or a phenyl or naphthyl radical; $R_4$ is alkyl, alkenyl, alkynyl, cycloalkyl, cycloalkenyl, bicycloalkyl, aryl, or heterocyclic radical; and $R^5$ is an optionally substituted cycloalkenyl, alkyl, alkenyl, alkynyl, or cycloalkyl radical. The compounds of formula (I), where Z is a formula (II) radical, have remarkable antitumoral and antineoplastic properties

11 Claims, No Drawings

TAXOIDS, THEIR PREPARATION AND PHARMACEUTICAL COMPOSITIONS CONTAINING THEM

This is a 371 application of PCT/FR95/01393 dated Oct. 23, 1995.

The present invention relates to new taxoids of general formula:

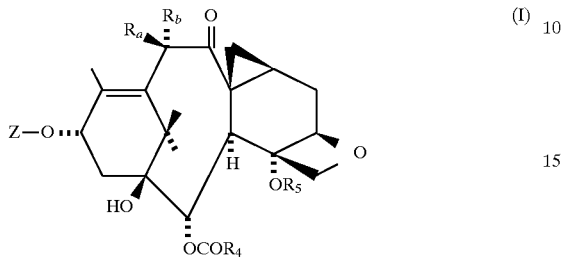

(I)

in which:
$R_a$ represents a hydrogen atom or a hydroxyl radical, an alkoxy radical containing 1 to 4 carbon atoms, an acyloxy radical containing 1 to 4 carbon atoms or an alkoxyacetoxy radical in which the alkyl portion contains 1 to 4 carbon atoms and $R_b$ represents a hydrogen atom, or alternatively $R_a$ and $R_b$, together with the carbon atom to which they are attached, form a keto function, Z represents a hydrogen atom or a radical of general formula:

(II)

in which:
$R_1$ represents a benzoyl radical optionally substituted with one or more identical or different atoms or radicals chosen from halogen atoms and alkyl radicals containing 1 to 4 carbon atoms, alkoxy radicals containing 1 to 4 carbon atoms or trifluoromethyl radicals, a thenoyl or furoyl radical or a radical $R_2$—O—CO— in which $R_2$ represents:
an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents chosen from halogen atoms and hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl portion contains 1 to 4 carbon atoms, a phenyl or α- or β-naphthyl radical optionally substituted with one or more atoms or radicals chosen from halogen atoms and alkyl radicals containing 1 to 4 carbon atoms or alkoxy radicals containing 1 to 4 carbon atoms, or a 5-membered aromatic heterocyclic radical preferably chosen from furyl and thienyl radicals, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, an aryl radical such as, a phenyl or α- or β-naphthyl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a heterocyclic radical, preferably a 5-membered aromatic heterocycle containing one or more identical or different hetero atoms chosen from nitrogen, oxygen and sulphur atoms and optionally substituted with one or more identical or different substituents chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, on the understanding that, in the substituents of the phenyl, α- or β-naphthyl and aromatic heterocyclic radicals, the alkyl radicals and the alkyl portions of the other radicals contain 1 to 4 carbon atoms, and that the alkenyl and alkynyl radicals contain 2 to 8 carbon atoms, and that the aryl radicals are phenyl or α- or β-naphthyl radicals, and $R_4$ represents
an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals being optionally substituted with one or more substituents chosen from halogen atoms and hydroxyl radicals, alkyloxy radicals containing 1 to 4 carbon atoms, dialkyamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, optionally substituted phenyl radicals, cyano or carboxyl radicals or alkoxycarbonyl radicals in which the alkyl portion contains 1 to 4 carbon atoms, or an aryl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxylalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro, azido, trifluoromethyl or trifluoromethoxy radicals, or a saturated or unsaturated 4- to 6-membered heterocyclic radical optionally substituted with one or more alkyl radicals containing 1 to 4 carbon atoms, and $R^5$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals being optionally substituted with one or more substituents chosen from halogen atoms and hydroxyl radicals, alky:Loxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, optionally substituted phenyl radicals, cyano or carboxyl radicals or alkyloxycarbonyl radicals in which the alkyl portion contains 1 to 4 carbon atoms, on the understanding that the cycloalkyl, cycloalkenyl or bicycloalkyl radicals may be optionally substituted with one or more alkyl radicals containing 1 to 4 carbon atoms.

Preferably, the aryl radicals which can be represented by $R_3$ and/or $R_4$ are phenyl or α- or β-naphthyl radicals optionally substituted with one or more atoms or radicals chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro, azido, trifluoromethyl and trifluoromethoxy radicals, on the understanding that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals.

Preferably, the heterocyclic radicals which can be represented by $R_3$ and/or $R_4$ are 5-membered aromatic heterocyclic radicals containing one or more identical or different atoms chosen from nitrogen, oxygen and sulphur atoms, optionally substituted with one or more identical or different substituents chosen from halogen atoms (fluorine, chlorine, bromine, iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 to 10 carbon atoms, cyano, carboxyl or carbamoyl radicals, alkylcarbamoyl radicals in which the alkyl portion contains 1 to 4 carbon atoms, dialkylcarbamoyl radicals in which each alkyl portion contains 1 to 4 carbon atoms or alkoxycarbonyl radicals in which the alkoxy portion contains 1 to 4 carbon atoms.

More especially, the present invention relates to the products of general formula (I) in which $R_a$ represents a hydroxyl radical, an alkoxy radical containing 1 to 4 carbon atoms, an acyloxy radical containing 1 to 4 carbon atoms or an alkoxyacetoxy radical in which the alkyl portion contains 1 to 4 carbon atoms and $R_b$ represents a hydrogen atom, Z represents a hydrogen atom or a radical of general formula (II) in which $R_1$ represents a benzoyl radical or a radical $R_2$—O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more identical or different atoms or radicals chosen from halogen atoms (fluorine, chlorine) and alkyl (methyl), alkoxy (methoxy), dialkylamino (dimethylamino), acylamino (acetylamino), alkoxycarbonylamino (tert-butoxycarbonylamino) or trifluoromethyl radicals, or a 2- or 3-furyl, 2- or 3-thienyl or 2-, 4- or 5-thiazolyl radical, and $R_4$ represents a phenyl radical optionally substituted with one or more identical or different atoms or radicals chosen from halogen atoms and alkyl, alkoxy, amino, alkylamino, dialkylamino, acylamino, alkoxycarbonylamino, azido, trifluoromethyl and trifluoromethoxy radicals, or a 2- or 3-thienyl or 2- or 3-furyl radical, and $R_5$ represents an optionally substituted alkyl radical containing 1 to 4 carbon atoms.

Still more especially, the present invention relates to the products of general formula (I) in which $R_a$ represents a hydrogen atom or a hydroxyl or acetyloxy or methoxyacetoxy radical and $R_b$ represents a hydrogen atom, Z represents a hydrogen atom or a radical of general formula (II) in which $R_1$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical and $R_4$ represents a phenyl radical optionally substituted with a halogen atom and $R_5$ represents an alkyl radical containing 1 to 4 carbon atoms.

The products of general formula (I) in which Z represents a radical of general formula (II) display noteworthy antitumour and antileukaemic properties.

According to the present invention, the products of general formula (I) in which $R_a$ represents a hydrogen atom or an alkoxy, acyloxy or alkoxyacetoxy radical, $R_b$ represents a hydrogen atom and $R_4$, $R_5$ and Z are defined as above may be obtained by the action of an alkali metal halide (sodium chloride, sodium iodide, potassium fluoride) or an alkali metal azide (sodium azide) or a quaternary ammonium salt or an alkali metal phosphate on a product of general formula:

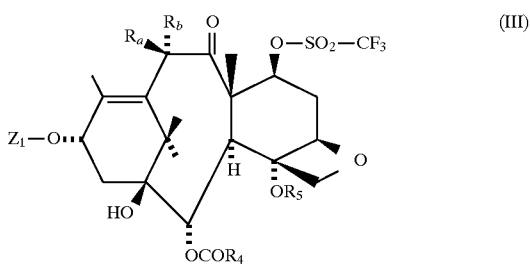

in which $Z_1$ represents a hydrogen atom or a radical of general formula (II) in which $R_1$ and $R_3$ are defined as above or a radical of general formula:

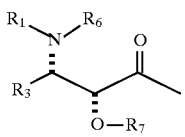

(IV)

in which $R_1$ and $R_3$ are defined as above, and either $R_6$ represents a hydrogen atom and $R_7$ represents a group protecting the hydroxyl function, or $R_6$ and $R_7$ together form a saturated 5- or 6-membered heterocycle, $R_4$ and $R_5$ are defined as above, $R_a$ represents a hydrogen atom or an alkoxy, acyloxy or alkoxyacetoxy radical or a protected hydroxyl radical, preferably a 2,2,2-trichloroethoxycarbonyloxy radical, and $R_b$ represents a hydrogen atom, or alternatively $R_a$ and $R_b$, together with the carbon atom to which they are attached, form a keto function, to obtain a product of general formula:

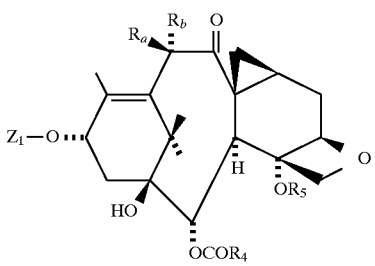

(V)

in which $Z_1$, $R_4$, $R_5$, $R_a$ and $R_b$ are defined as above, followed, if necessary, by replacement of the protective group borne by $R_a$ or of the protective groups represented by $R_7$ and/or by $R_6$ and $R_7$ by the hydrogen atoms.

Generally, the reaction is performed in an organic solvent chosen from ethers (tetrahydrofuran, diisopropyl ether, methyl, tert-butyl ether) and nitriles (acetonitrile), alone or mixed, at a temperature between 20° C. and the boiling point of the reaction mixture.

A product of general formula (V) in which $Z_1$ represents a hydrogen atom or a radical of general formula (II), $R_a$ represents a hydrogen atom or a hydroxyl radical, an alkoxy radical containing 1 to 4 carbon atoms, an acyloxy radical containing 1 to 4 carbon atoms or an alkoxyacetoxy radical in which the alkyl portion contains 1 to 4 carbon atoms and $R_b$ represents a hydrogen atom, or alternatively $R_a$ and $R_b$, together with the carbon atom to which they are attached, form a keto function, is identical to a product of general formula (I).

In the general formula (V), when $Z_1$ represents a radical of general formula (IV) and when $R_6$ represents a hydrogen atom, $R_7$ preferably represents a methoxymethyl, 1-ethoxyethyl, benzyloxymethyl, trimethylsilyl, triethylsilyl, β-trimethylsilylethoxymethyl, benzyloxycarbonyl or tetrahydropyrranyl radical, or alternatively, when $R_6$ and $R_7$ together form a heterocycle, the latter is preferably an oxazolidine ring optionally monosubstituted or gem-disubstituted at position 2.

Replacement of the protective groups $R_7$ and/or $R_6$ and $R_7$ by hydrogen atoms, and where appropriate of $R_a$ by a hydroxyl radical, may be performed, depending on their nature, in the following manner:

1) when $R_6$ represents a hydrogen atom and $R_7$ represents a group protecting the hydroxyl function, and $R_a$ represents an alkoxy, acyloxy or alkoxyacetoxy radical, replacement of the protective groups by hydrogen atoms is performed by means of an inorganic acid (hydrochloric acid, sulphuric acid, hydrofluoric acid) or organic acid (acetic acid, methanesulphonic acid, trifluoromethanesulphonic acid, p-toluenesulphonic acid) used alone or mixed, working in an organic solvent chosen from alcohols, ethers, esters, aliphatic hydrocarbons, halogenated aliphatic hydrocarbons, aromatic hydrocarbons or nitriles at a temperature of between −10° and 60° C., 2) when $R_6$ represents a hydrogen atom and $R_7$ represents a group protecting the hydroxyl function, and $R_a$ represents a 2,2,2-trichloroethoxycarbonyloxy radical, replacement of the protective group $R_7$ is performed under the conditions described above under 1) and that of $R_a$ by treatment with zinc, optionally in combination with copper, in the presence of acetic acid at a temperature of between 30° and 60° C., or by means of an inorganic or organic acid such as hydrochloric acid or acetic acid in solution in an aliphatic alcohol containing 1 to 3 carbon atoms (methanol, ethanol, propanol, isopropanol) or in an aliphatic ester (ethyl acetate, isopropyl acetate, n-butyl acetate) in the presence of zinc, optionally in combination with copper, 3) when $R_6$ and $R_7$ together form a 5- or 6-membered saturated heterocycle, and more especially an oxazolidine ring of general formula:

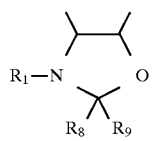

(VI)

in which $R_1$ is defined as above and $R_8$ and $R_9$, which may be identical or different, represent a hydrogen atom or an alkyl radical containing 1 to 4 carbon atoms, or an aralkyl radical in which the alkyl portion contains 1 to 4 carbon atoms and the aryl portion preferably represents a phenyl radical optionally substituted with one or more alkoxy radicals containing 1 to 4 carbon atoms, or an aryl radical preferably representing a phenyl radical optionally substituted with one or more alkoxy radicals containing 1 to 4 carbon atoms, or alternatively $R_8$ represents an alkoxy radical containing 1 to 4 carbon atoms or a trihalomethyl radical such as trichloromethyl or a phenyl radical substituted with a trihalomethyl radical such as trichloromethyl and $R_9$ represents a hydrogen atom, or alternatively $R_8$ and $R_9$, together with the carbon atom to which they are attached, form a 4- to 7-membered ring, and $R_a$ represents an acyloxy or alkoxyacetoxy or 2,2,2-trichloroethoxycarbonyloxy radical, replacement of the protective group formed by $R_6$ and $R_7$ by hydrogen atoms and of $R_a$ by a hydroxyl radical may be performed, depending on the meanings of $R_a$, $R_1$, $R_8$ and $R_9$, in the following manner:

a) when $R_1$ represents a tert-butoxycarbonyl radical and $R_8$ and $R_9$, which may be identical or different, represent an alkyl radical or an aralkyl (benzyl) or aryl (phenyl) radical, or alternatively $R_8$ represents a trihalomethyl radical or a phenyl radical substituted with a trihalomethyl radical and $R_9$ represents a hydrogen atom, or alternatively $R_8$ and $R_9$ together form a 4- to 7-membered ring, treatment of the ester of general formula (V) with an inorganic or organic acid, where appropriate in an organic solvent such as an alcohol, yields the product of general formula:

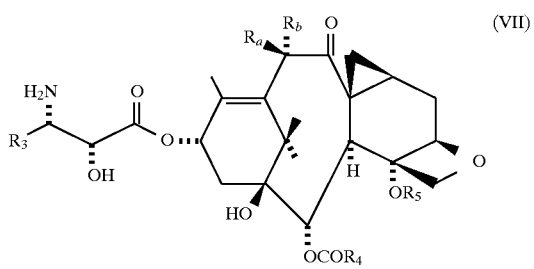
(VII)

in which $R_a$, $R_b$, $R_3$, $R_4$ and $R_5$ are defined as above, which is acylated by means of benzoyl chloride in which the phenyl ring is optionally substituted or by means of thenoyl chloride, of furoyl chloride or of a product of general formula:

$$R_2-O-CO-X \quad (VIII)$$

in which $R_2$ is defined as above and X represents a halogen atom (fluorine, chlorine) or a residue $-O-R_2$ or $-O-CO-O-R_2$, to obtain a product of general formula:

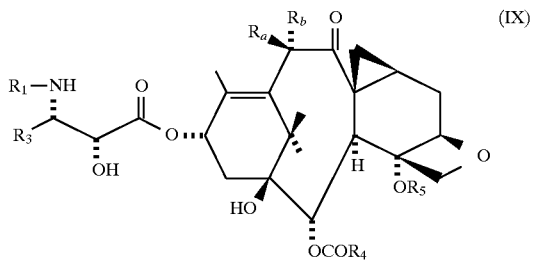
(IX)

in which $R_a$, $R_b$, $R_1$, $R_3$, $R_4$ and $R_5$ are defined as above, in which the protective group $R_a$, when it represents a protected hydroxyl radical, is replaced, if necessary, by a hydroxyl radical.

Preferably the product of general formula (V) is treated with formic acid at a temperature in the region of 20° C.

Preferably, the acylation of the product of general formula (VII) by means of a benzoyl chloride in which the phenyl radical is optionally substituted or by means of thenoyl chloride, of furoyl chloride or of a product of general formula (VIII) is performed in an inert organic solvent chosen from esters such as ethyl acetate, isopropyl acetate or n-butyl acetate and halogenated aliphatic hydrocarbons such as dichloromethane or 1,2-dichloroethane, in the presence of an inorganic base such as sodium bicarbonate or an organic base such as triethylamine. The reaction is performed at a temperature of between 0° and 50° C., and preferably in the region of 20° C.

Preferably, replacement of the protective group $R_a$, when it represents a 2,2,2-trichloroethoxycarbonyloxy radical, is performed under the conditions described above under 2).

b) when $R_1$ represents an optionally substituted benzoyl radical, a thenoyl or furoyl radical or a radical $R_2-O-CO$ in which $R_2$ is defined as above, $R_8$ represents a hydrogen atom or an alkoxy radical containing 1 to 4 carbon atoms or a phenyl radical substituted with one or more alkoxy radicals containing 1 to 4 carbon atoms and $R_9$ represents a hydrogen atom, replacement of the protective group formed by $R_6$ and $R_7$ by hydrogen atoms is performed in the presence of an inorganic acid (hydrochloric acid, sulphuric acid) or organic acid (acetic acid, methanesulphonic acid, trifluoromethanesulphonic acid, p-toluenesulphonic acid) used alone or mixed in a stoichiometric or catalytic amount, working in an organic solvent chosen from alcohols, ethers, esters, aliphatic hydrocarbons, halogenated aliphatic hydrocarbons and aromatic hydrocarbons at a temperature of between −10° and 60° C., and preferably between 15° and 30° C., and replacement of the protective group $R_a$, when it represents a 2,2,2-trichloroethoxycarbonyloxy radical, by a hydrogen atom is performed under the conditions described above under 2).

4) when $R_a$ represents an alkoxyacetyl radical and $R_6$ and $R_7$ are defined as in point 1) above, replacement of the protective group $R_7$ by a hydrogen atom is first performed by working under the acid conditions described in point 1) above, and $R_a$ is then replaced, where appropriate, by a hydroxyl radical by treatment in an alkaline medium or by the action of a zinc halide under conditions which do not affect the remainder of the molecule. Generally, the alkaline treatment is performed by the action of ammonia in an acqueous-alcoholic medium or of hydrazine hydrate in an alcoholic medium at a temperature in the region of 20° C. Generally, the treatment with a zinc halide, preferably zinc iodide, is performed in methanol at a temperature in the region of 20° C.

5) when $R_a$ represents an alkoxyacetoxy radical and $R_6$ and $R_7$ are defined as in point 3-a) above, replacement of the radical $R_a$ by a hydroxyl radical is performed by treatment in an alkaline medium or by treatment with a zinc halide under the conditions described in point 4) above, and the product of general formula (VI) obtained is then treated under the deprotection and acylation conditions described in point 3-a) above.

6) when $R_a$ represents an alkoxyacetoxy radical and $R_6$ and $R_7$ are defined as in point 3-b) above, replacement of the radical $R_a$ by a hydroxyl radical is performed by treatment in an alkali medium or by treatment with a zinc halide under the conditions described in point 4) above, and the product obtained is then treated under the conditions described in point 3-b) above.

The product of general formula (III) in which $Z_1$ represents a radical of general formula (II) or a radical of general formula (IV) may be obtained by esterification of a product of general formula:

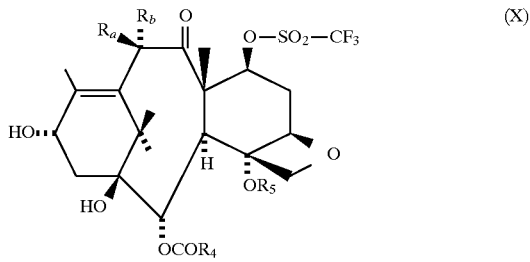
(X)

in which $R_4$ and $R_5$ are defined as above, and $R_a$ represents a hydrogen atom or an alkoxy, acyloxy or alkoxyacetoxy radical or a protective hydroxyl radical, and $R_b$ represents a hydrogen atom, by means of an acid of general formula:

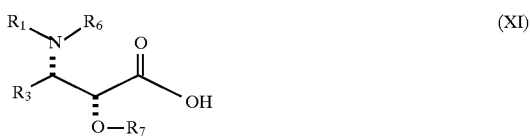
(XI)

in which $R_1$ and $R_3$ are defined as above, either $R_6$ represents a hydrogen atom and $R_7$ represents a group protecting the hydroxyl function, and or $R_6$ and $R_7$ together form a saturated 5- or 6-membered heterocycle, or a derivative of this acid, to obtain an ester of general formula:

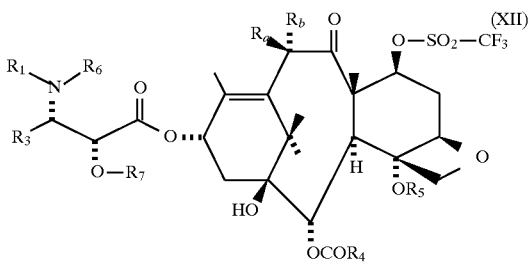

in which $R_a$, $R_b$, $R_1$, $R_3$, $R_4$, $R_5$, $R_6$ and $R_7$ are defined as above, followed, if necessary, by replacement of the protective groups represented by $R_7$ and/or $R_6$ and $R_7$ by hydrogen atoms, and, where appropriate, $R_a$ when it represents an acyloxy or alkoxyacetoxy radical or a protected hydroxyl radical, by a hydroxyl radical, under the conditions described above for replacement of the protective groups of the product of general formula (V) in which $Z_1$ represents a radical of general formula (IV).

The esterification by means of an acid of general formula (XI) may be performed in the presence of a condensing agent (carbodiimide, reactive carbonate) and an activating agent (aminopyridines) in an organic solvent (ether, ester, ketones, nitriles, aliphatic hydrocarbons, halogenated aliphatic hydrocarbons, aromatic hydrocarbons) at a temperature of between −10° and 90° C.

The esterification may also be carried out using the acid of general formula (XI) in an anhydride form, working in the presence of an activating agent (aminopyridines) in an organic solvent (ethers, esters, ketones, nitriles, aliphatic hydrocarbons, halogenated aliphatic hydrocarbons, aromatic hydrocarbons) at a temperature of between 0° and 90° C.

The esterification may also be carried out using the acid of general formula (XI) in halide form or in anhydride form with an aliphatic or aromatic acid, optionally prepared in situ, in the presence of a base (tertiary aliphatic amine), working in an organic solvent (ethers, esters, ketones, nitriles, aliphatic hydrocarbons, halogenated aliphatic hydrocarbons, aromatic hydrocarbons) at a temperature of between 0° and 80° C.

According to the invention, the products of general formula (III) in which $R_4$ and $R_5$ are defined as above, $R_a$ represents a hydrogen atom or an alkoxy, acyloxy or alkoxyacetoxy radical, $R_b$ represents a hydrogen atom and $Z_1$ represents a hydrogen atom may be obtained by the action of a trifluoromethanesulphonic acid derivative such as the anhydride or N-phenyltrifluoromethanesulphonimide on a product of general formula:

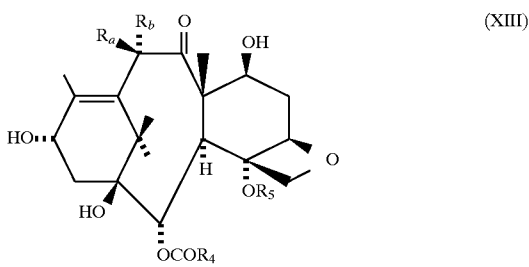

in which $R_a$, $R_b$, $R_4$ and $R_5$ are defined as above.

Generally, the reaction is performed in an inert organic solvent (aliphatic hydrocarbons, optionally halogenated, aromatic hydrocarbons) in the presence of an organic base such as a tertiary aliphatic amine (triethylamine) or pyridine at a temperature of between −50° and +20° C.

The products of general formula (XIII) in which $R_4$ and $R_5$ are defined as above, $R_a$ represents a hydrogen atom or an alkoxy, acyloxy or alkoxyacetoxy radical or a protected hydroxyl radical and $R_b$ represents a hydrogen atom may be obtained by the action of hydrofluoric acid or trifluoroacetic acid in a basic organic solvent such as pyridine optionally substituted with one or more alkyl radicals containing 1 to 4 carbon atoms, or triethylamine optionally in combination with an inert organic solvent such as methylene chloride or acetonitrile or tetrahydrofuran, at a temperature of between 20° and 80° C., on a product of general formula:

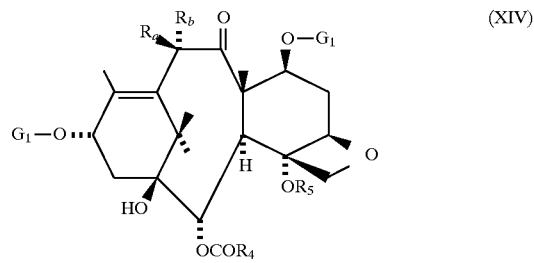

in which $R_4$ and $R_5$ are defined as above, $R_a$ represents a hydrogen atom or an alkoxy, acyloxy or alkoxyacetoxy radical or a protected hydroxyl radical, $R_b$ represents a hydrogen atom and the symbols $G_1$, which are identical, represent a trialkylsilyl radical.

The product of general formula (XIV) in which $R_a$ represents an alkoxy, acyloxy or alkoxyacetoxy radical or a protected hydroxyl radical and $R_b$ represents a hydrogen atom may be obtained by the action of a product of general formula:

R—Y (XV)

in which R represents an alkyl, alkanoyl or alkoxyacetyl radical or a group protecting the hydroxyl function and Y represents a halogen atom, on a product of general formula:

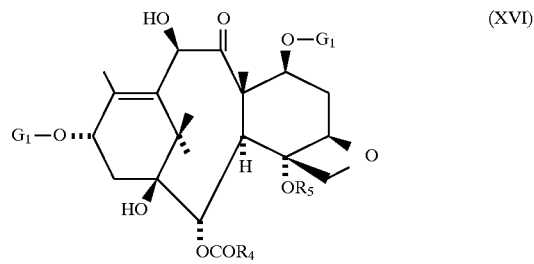

in which $R_4$, $R_5$ and $G_1$ are defined as above.

When R represents an alkanoyl or alkoxyacetyl radical, it is especially advantageous to work in a basic organic solvent such as pyridine or in an inert organic solvent such as methylene chloride, chloroform or 1,2-dichloroethane, in the presence of a tertiary amine such as triethylamine or pyridine at a temperature in the region of 0° C.

When R represents an alkyl radical, it is especially advantageous to metalate the hydroxyl function on a secondary carbon atom beforehand by means of an alkali metal hydride (sodium hydride) or a metal alkyl (butyllithium).

The product of general formula (XVI), and where appropriate the product of general formula (XIV), may be obtained by the action of an organometallic derivative of general formula:

$R_4$—M (XVII)

in which $R_4$ is defined as above and M represents a metal atom, preferably a lithium or magnesium atom, on a product of general formula:

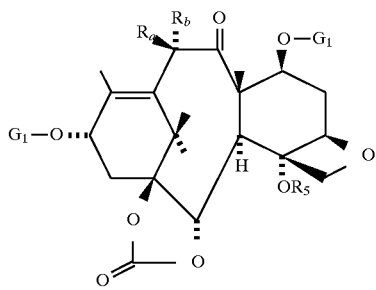

(XVIII)

in which $R_a$, $R_b$, $R_5$ and $G_1$ are defined as above.

Generally, the reaction is performed in an organic solvent such as an ether (tetrahydrofuran) at a temperature below −50° C., preferably in the region of −78° C.

The product of general formula (XVIII) may be obtained by etherification of a product of general formula:

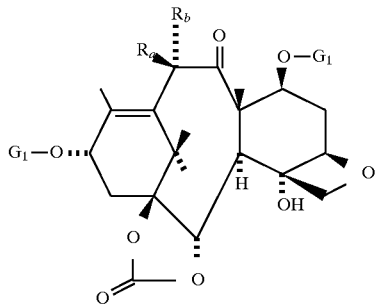

(XIX)

in which $R_a$, $R_b$ and $G_1$ are defined as above, by means of a halide of general formula:

$R_5$—Hal       (XX)

in which $R_5$ is defined as above and Hal represents a halogen atom.

It is especially advantageous to metalate the tertiary hydroxyl function of the product of general formula (XIX) by the action of an alkali metal hydride or amide such as sodium hydride of lithium diisopropylamide prior to the action of the product of general formula (XX).

Generally, the reaction is performed in a polar organic solvent such as dimethylformamide at a temperature of between 0° and 50° C.

The product of general formula (XIX) may be obtained by the action of a product of general formula (XV) on a product of general formula:

(XXI)

in which $G_1$ is defined as above, under the conditions described above for the action of a product of general formula (XV) on a product of general formula (XVI).

The product of general formula (XXI) may be prepared by the action of phosgene or one of its derivatives, such as triphosgene, on a product of general formula:

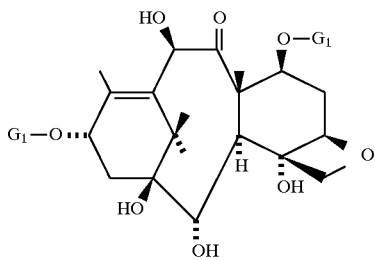

(XXII)

in which $G_1$ is defined as above, working in a basic organic solvent such as pyridine at a temperature below −50° C., preferably in the region of −78° C.

The product of general formula (XXII) may be prepared by the action of a halotrialkylsilane on a product of general formula:

(XXII)

in which $G_1$ is defined as above, working in a basic organic solvent.

The product of general formula (XXIII) may be prepared under the conditions described by D. G. I. Kingston et al., Journal of Nat. Prod., 56, 884 (1993), incorporated herein by reference.

The products of general formula (XIV) in which $R_4$ represents a phenyl radical, $R_5$ is defined as above, $R_a$ represents a hydrogen atom or a hydroxyl, alkoxy, acyloxy or alkoxyacetoxy radical or a protected hydroxyl radical and $R_b$ represents a hydrogen atom may be obtained by the action of a product of general formula (XX) on a product of general formula:

(XXIV)

in which $R_a$ and $R_b$ are defined as above and $G_1$ is defined as above, under the conditions described above for the action of a product of general formula (XX) on a product of general formula (XIX).

The products of general formula (XXIV) in which $R_a$ represents a group protecting the hydroxyl function which is identical to $G_1$ and $R_b$ represents a hydrogen atom may be obtained by the action of a halotrialkylsilane on a product of general formula:

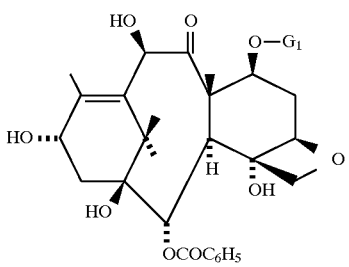

(XXV)

in which $G_1$ is defined as above.

The reaction is preferably performed in an organic solvent such as dimethylformamide in the presence of imidazole.

The products of general formula (XXIV) in which $R_a$ represents an alkoxy, acyloxy or alkoxyacetoxy radical, $R_b$ represents a hydrogen atom and $G_1$ is defined as above may be obtained by the action of a product of general formula (XV) on a product of general formula:

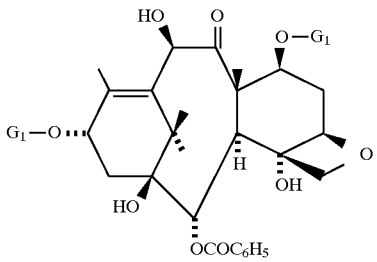

(XXVI)

in which $G_1$ is as defined above, under the conditions described above for the action of a product of general formula (XV) on a product of general formula (XVI).

The products of general formula (XXVI) may be obtained by the action of a halotrialkylsilane on a product of general formula (XXV) under the conditions described above for the action of a halotrialkylsilane of a product of general formula (XXIII).

The products of general formula (XXV) may be obtained under the conditions described by D. G. I. Kingston et al., Tetrahedron Letters, 35, 6839 (1992), incorporated herein by reference.

The products of general formula (I) in which $R_a$ and $R_b$ each represent a hydrogen atom may be obtained by electrolytic reduction of a product of general formula (I) in which $R_a$ represents a hydroxyl radical or an acyloxy or alkoxyacetoxy radical, or under the conditions described in International Application PCT WO 93/06093, incorporated herein by reference.

The products of general formula (I) in which $R_a$ and $R_b$, together with the carbon atom to which they are attached, form a keto function may be obtained by oxidation of a product of general formula (I) in which $R_a$ represents a hydroxyl radical and $R_b$ represents a hydrogen atom, by means, for example, of pyridinium chlorochromate, pyridinium dichromate, potassium dichromate, ammonium dichromate or manganese dioxide.

The new products of general formula (I) obtained by carrying out the processes according to the invention may be purified according to known methods such as crystallization or chromatography.

The products of general formula (I) in which Z represents a radical of general formula (II) display noteworthy biological properties.

In vitro, measurement of the biological activity is performed on tubulin extracted from pig's brain by the method of M. L. Shelanski et al., Proc. Natl. Acad. Sci. USA, 70, 765–768 (1973). Study of the depolymerization of microtubules to tubulin is performed according to the method of G. Chauvière et al., C.R. Acad. Sci., 293, series II, 501–503 (1981). In this study, the products of general formula (I) in which Z represents a radical of general formula (II) were shown to be at least as active as taxol and Taxotere.

In vivo, the products of general formula (I) in which Z represents a radical of general formula (II) were shown to be active in mice grafted with B16 melanoma at doses of between 1 and 10 mg/kg administered intraperitoneally, as well as on other liquid or solid tumours.

The new products have antitumour properties, and more especially activity against tumours which are resistant to Taxol® or to Taxotere®. Such tumours comprise colon tumours which have a high expression of the mdr 1 gene (multiple drug resistance gene). Multiple drug resistance is a customary term relating to the resistance of a tumour to different products having different structures and mechanisms of action. Taxoids are generally known to be strongly recognized by experimental tumours such as P388/DOX, a cell line selected for its resistance to doxorubicin (DOX) which overexpresses mdr 1.

The examples which follow illustrate the present invention.

EXAMPLE 1

A solution of 40 mg of 2α-benzoyloxy-1β,10β-dihydroxy-5β,20-epoxy-4α-methoxy-7β,8-methylene-19-nor-9-oxo-11-taxen-13α-yl (2R,4S,5R)-3-tert-butoxycarbonyl-2-(4-methoxyphenyl)-4-phenyl-1,3-oxazolidine-5-carboxylate in 450 μl of a 0.1N solution of hydrogen chloride in ethanol is kept stirring at a temperature in the region of 0° C. for 3 hours. The reaction mixture is concentrated to dryness under reduced pressure (2.7 kPa) at 20° C. The crude product obtained is dissolved in 10 cm³ of dichloromethane and 10 cm³ of saturated aqueous sodium bicarbonate solution. The organic phase is separated after settling has taken place, washed with 2 times 10 cm³ of saturated aqueous sodium chloride solution, then dried over magnesium sulphate, filtered and concentrated to dryness under reduced pressure (2.7 kPa) at 40° C. 59 mg of a product are obtained, which product is purified by preparative chromatography on a silica plate 0.5 mm thick, eluting with a cyclohexane/ethyl acetate (60:40 by volume) mixture. 12 mg of 2α-benzoyloxy-1β,10β-dihydroxy-5β,20-epoxy-4α-methoxy-7β,8-methylene-19-nor-9-oxo-11-taxen-13α-yl (2R,3S)-3-tert-butoxycarbonylamino-2-hydroxy-3-phenylpropionate are thereby obtained in the form of a white foam, the physical characteristics of which are as follows:

proton NMR spectrum (400 MHz; CDCl₃; δ in ppm; coupling constants J in Hz); 1.20 (s, 6H: CH₃); 1.35 (s, 9H: C(CH₃)₃); from 1.35 to 1.60 (mt, 1H: H at position 7); 1.73 (s, 1H: OH at position 1); 1.81 and 2.27 (2 mts, 1H each: CH₂ at position 19); 1.90 (s, 3H: CH₃); 2.07 and 2.26 (2 mts, 1H each: CH₂ at position 6); 2.35 and 2.87 (2 mts, 1H each: CH₂ at position 14); 3.24 (mt, 1H: OH at position 2'); 3.46 (s, 3H: OCH₃); 3.70 (d, J=7, 1H: H at position 3); 3.97 and 4.39 (2 d, J=9, 1H each: CH₂ at position 20); 4.24 (broad s, 1H: OH at position 10); 4.62 (mt, 1H: H at position 2'); 4.90 (broad d, J=4, 1H: H at position 5); 4.98 (s, 1H: H at position 10); 5.36 (mt, 1H: H at position 3'); 5.48 (d, J=10, 1H: CONH); 5.69 (d, J=7, 1H: H at position 2); 6.24 (mt, 1H: H at position 13); from 7.25 to 7.50 (mt, 5H: aromatic H at position 3'); 7.49 (t, J=7.5, 2H: OCOC₆H₅ H at the meta position); 7.57 (t, J=7.5, 1H: OCOC₆H₅ H at the para position); 8.12 (d, J=7.5, 2H: OCOC₆H₅ H at the ortho position).

2α-Benzoyloxy-1β,10β-dihydroxy-5β,20-epoxy-4α-methoxy-7β,8-methylene-19-nor-9-oxo-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

100 mg of powdered 4 Å molecular sieves and 100 mg of sodium azide are added successively to a solution of 112 mg of 2α-benzoyloxy-1β,10β-dihydroxy-5β,20-epoxy-4α-methoxy-9-ox-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate in 1 cm³ of acetonitrile and 0.1 cm³ of tetrahydrofuran. The reaction mixture is kept stirring at a temperature in the region of 75° C. for 3 hours, and 50 cm³ of dichloromethane and 50 cm³ of saturated aqueous sodium chloride solution are then added at a temperature in the region of 20° C. The organic phase is separated after settling has taken place, washed with 2 times 40 cm³ of saturated aqueous sodium chloride solution, then dried over magnesium sulphate, filtered and concentrated to dryness under reduced pressure (2.7 kPa) at 40° C. 77 mg of a product are obtained, which product is purified by preparative chromatography on a silica plate 2 mm thick, eluting with a dichloromethane/methanol (90:10 by volume) mixture. 45 mg of 2α-benzoyloxy-1β,10β-dihydroxy-5β,20-epoxy-4α-methoxy-7β,8-methylene-19-nor-9-oxo-11-taxen-13-yl (2R,4S,5R)-3-tert-butyoxycarbonyl-2-(4-methoxyphenyl)-4-phenyl-1,3-oxazolidine-5-carboxylate are thereby obtained in the form of a white foam, the physical characteristics of which are as follows:

proton NMR spectrum (400 MHz; $CDCl_3$; at a temperature of 330° K.; δ in ppm; coupling constants J in Hz): 1.10 (s, 9H: $C(CH_3)_3$); 1.20 (s, 3H: $CH_3$); 1.22 (s, 3H: $CH_3$); 1.29 (mt, 1H: H at position 7); 1.68 (s, 3H: $CH_3$); 1.78 and from 2.25 to 2.35 (2 mts, 1H each: $CH_2$ at position 19); 1.99 and 2.24 (dt and broad d, respectively, J=17 and 4 and J=17, 1H each: $CH_2$ at position 6); from 2.25 to 2.35 and 2.56 (mt and dd, respectively (J=15 and 7), 1H each: $CH_2$ at position 14); 3.06 (s, 3H: $OCH_3$); 3.67 (d, J=7, 1H: H at position 3); 3.80 (s, 3H: $ArOCH_3$); 3.96 and 4.26 (2d, J=9, 1H each: $CH_2$ at position 20); 4.17 (broad s, 1H: OH at position 10); 4.66 (d, J=5, 1H: H at position 2'); 4.78 (broad d, J=4, 1H: H at position 5); 4.92 (broad s, 1H: H at position 10); 5.48 (mt, 1H: H at position 3'); 5.66 (d, J=7, 1H: H at position 2); 6.05 (mt, 1H: H at position 13); 6.38 (s, 1H: H at position 5'); 6.91 (d, J=8.5, 2H: aromatic H at the ortho position with respect to $OCH_3$); from 7.30 to 7.50 (mt, 7H: aromatic H at position 3' and $OCOC_6H_5$ H at the meta position); 7.41 (d, J=8.5, 2H: aromatic H at the meta position with respect to $OCH_3$); 7.58 (t, J=7.5, 1H: $OCOC_6H_5$ H at the para position); 7.96 (d, J=7.5, 2H: $OCOC_6H_5$ H at the ortho position).

2α-Benzoyloxy-1β,10β-dihydroxy-5β,20-epoxy-4α-methoxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

70 mg of (2R,4S,5R)-3-tert-butoxycarbonyl-2-(4-methoxyphenyl)-4-phenyl-1,3-oxazolidine-5-carboxylic acid, 50 mg of dicyclohexylcarbodiimide and 6 mg of 4-(methylamino)pyridine are added successively at a temperature in the region of 20° C. to a solution of 100 mg of 2α-benzoyloxy-5β,20-epoxy-4α-methoxy-9-oxo-7β-trifluoromethanesulphonyloxy-1β,10β,13α-trihydroxy-11-taxene in 4 cm³ of anhydrous ethyl acetate. The reaction mixture is stirred for 3 hours and 30 minutes under an argon atmosphere at a temperature in the region of 20° C. 30 cm³ of ethyl acetate and 20 cm³ of saturated aqueous ammonium chloride solution are added. The organic phase is separated after settling has taken place, washed with 2 times 20 cm³ of water and then dried over magnesium sulphate. After filtration and concentration to dryness under reduced pressure (2.7 kPa) at 40° C., 200 mg of a product are obtained, which product is purified by chromatography on 15 g of silica (0.063–0.2 mm) contained in a column 1 cm in diameter, eluting with a cyclohexane/ethyl acetate (80:20 by volume) mixture, collecting 8 cm³ fractions. Fractions containing only the desired product are pooled and concentrated to dryness under reduced pressure (2.7 kPa) at 40° C. 112 mg of 2α-benzoyloxy-1β,10β-dihydroxy-5β,20-epoxy-4α-methoxy-9-oxo-7β-trifluoromethanesulphonyloxy-11-taxen-13α-yl (2R,4S,5R)-3-tert-butoxycarbonyl-2-(4methoxyphenyl)-4-phenyl-1,3-oxazolidine-5-carboxylate are thereby obtained in the form of a white foam, the physical characteristics of which are as follows:

proton NMR spectrum (400 MHz; $CDCl_3$; at a temperature of 333° K.; δ in ppm; coupling constants J in Hz): 1.10 (s, 9H: $C(CH_3)_3$); 1.13 (s, 3H: $CH_3$); 1.18 (s, 3H: $CH_3$); 1.77 (s, 3H: $CH_3$); 1.87 (s, 3H: $CH_3$); 2.33 and 2.76 (2 dd, J=15 and 11 Hz and J=15 and 7, 1H each: $CH_2$ at position 14); 2.36 and 2.68 (2 mts, 1H each: $CH_2$ at position 6); 3.19 (s, 3H: $OCH_3$); 3.44 (d, J=6, 1H: H at position 3); 3.83 (s, 3H: $ArOCH_3$); 3.95 (broad s, 1H: OH at position 10); 4.19 and 4.34 (2d, J=9, 1H each: $CH_2$ at position 20); 4.66 (d, J=5.5, 1H: H at position 2'); from 4.85 to 4.95 (mt, 2H: H at position 7 and H at position 5); 5.32 (broad s, 1H: H at position 10); 5.49 (d, J=5.5, 1H: H at position 3'); 5.60 (d, J=6, 1H: H at position 2); 5.95 (mt, 1H: H at position 13); 6.38 (s, 1H: H at position 5'); 6.94 (d, J=8.5, 2H: aromatic H at the ortho position with respect to $OCH_3$); from 7.30 to 7.50 (mt, 7H: aromatic H at position 3' and $OCOC_6H_5$ H at the meta position); 7.40 (d, J=8.5, 2H: aromatic H at the meta position with respect to $OCH_3$); 7.60 (t, J=7.5, 1H: $OCOC_6H_5$ H at the para position); 7.97 (d, J=7.5, 2H: $OCOC_6H_5$ H at the ortho position).

2α-Benzoyloxy-5β,20-epoxy-4α-methoxy-9-oxo-7β-trifluoromethanesulphonyloxy-1β,10β,13α-trihydroxy-11-taxene may be prepared in the following manner:

25 μl of triflic anhydride are added at a temperature in the region of 0° C. to a solution of 51.6 mg of 2α-benzoyloxy-5β,20-epoxy-4α-methoxy-9-oxo-1β,7β,10β,13α-tetrahydroxy-11-taxene in 0.5 cm³ of dichloromethane and 24 μl of pyridine. The reaction mixture is stirred for 20 minutes at a temperature in the region of 0° C., and 15 cm³ of dichloromethane and 3 cm³ of water are then added. The organic phase is separated after settling has taken place, washed with 2 times 10 cm³ of saturated aqueous ammonium chloride solution, then dried over magnesium sulphate. After filtration and concentration to dryness under reduced pressure (2.7 kPa) at 20° C., 72 mg of a product are obtained, which product is purified by chromatography on a silica plate 2 mm thick, eluting with a dichloromethane/methanol (90:10 by volume) mixture. 8 mg of 2α-benzoyloxy-5β,20-epoxy-4α-methoxy-1β,10β,13α-trihydroxy-9-oxo-7β-trifluoromethanesulphonyloxy-11-taxene are thereby obtained in the form of a white foam, the physical characteristics of which are as follows:

proton NMR spectrum (400 MHz; $CDCl_3$; δ in ppm; coupling constants J in Hz): 1.06 (s, 3H:$CH_3$); 1.10 (s, 3H: $CH_3$); 1.86 (s, 3H: $CH_3$); 2.13 (s, 3H: $CH_3$); 2.41 and 2.74 (2 mts, 1H each: $CH_2$ at position 6); 2.47 and 2.59 (2 dd, J=16 and 10 and J=16 and 4, 1H each: $CH_2$ at position 14); 2.96 (broad d, J=10, 1H: OH at position 13); 3.66 (s, 3H: OCH$_3$); 3.79 (d, J=6, 1H: H at position 3); 3.95 (broad s, 1H: OH at position 10); 4.30 and 4.49 (2d, J=9, 1H each: CH$_2$ at position 20); 4.57 (mt, 1H: H at position 13); 4.98 (dd, J=12 and 6, 1H: H at position 7); 5.04 (dd, J=10 and 3, 1H: H at position 5); 5.42 (broad s, 1H: H at position 10); 5.61 (d, J=6, 1H: H at position 2); 7.59 (t, J=7.5, 2H: OCOC$_6$H$_5$ H at the meta position); 7.63 (t, J=7.5, 1H: OCOC$_6$H$_5$ H at the para position); 8.00 (d, J=7.5, 2H: OCOC$_6$H$_5$ H at the ortho position).

2α-Benzoyloxy-5β,20-epoxy-4α-methoxy-9-oxo-1β,7β,10β,13α-tetrahydroxy-11-taxene may be prepared in the following manner:

7.5 cm$^3$ of triethylamine-hydrofluoric acid complex are added at a temperature in the region of 20° C. to a solution of 338 mg of 2α-benzoyloxy-1β,10β,-dihydroxy-7β,13α-ditriethylsilyloxy-5β,20-epoxy-4α-methoxy-9-oxo-11-taxene in 5 cm$^3$ of trichloromethane. The reaction mixture is stirred for 2 hours at a temperature in the region of 20° C. and 50 cm$^3$ of dichloromethane and 50 cm$^3$ of saturated aqueous sodium hydrogen carbonate solution are then added. The organic phase is separated after settling has taken place, washed with 2 times 50 cm$^3$ of saturated aqueous sodium chloride solution and then dried over magnesium sulphate. After filtration and concentration to dryness under reduced pressure (2.7 kPa) a 40° C., 420 mg of a product are obtained, which product is purified by chromatography on 60 g of silica (0.063–0.2 mm) contained in a column 1 cm in diameter, eluting with a dichloromethane/methanol (95:5 by volume) mixture, collecting 10 cm$^3$ fractions. Fractions containing only the desired product are pooled and concentrated to dryness under reduced pressure (2.7 kPa) at 40° C. 184 mg of 2α-benzoyloxy-5β,20-epoxy-4α-methoxy-9-oxo-1β,7β,10β,13α-tetrahydroxy-11-taxene are thereby obtained in the form of a white foam, the physical characteristics of which are as follows:

proton NMR spectrum (400 MHz; CDCl$_3$; δ in ppm; coupling constances J in Hz): 1.05 (s, 3H: CH$_3$); 1.10 (s, 3H: CH$_3$); 1.72 (s, 3H: CH$_3$); 1.99 and from 2.40 to 2.55 (2 mts, 1H each: CH$_2$ at position 6); 2.09 (s, 3H: CH$_3$); 2.48 and 2.69 (2 dd, J=16 and 10 and J=16 and 4, 1H each: CH$_2$ at position 14); 3.15 (broad d, J=11, 1H: OH at position 13); 3.65 (s, 3H: OCH$_3$); 3.74 (d, J=6, 1H: H at position 3); 3.78 (dd, J=12 and 6, 1H: H at position 7); 4.13 (broad s, 1H: OH at position 10); 4.31 and 4.45 (2 d, J=9.5, 1H each: CH$_2$ at position 20); 4.54 (mt, 1H: H at position 13); 5.00 (dd, J=10 and 3, 1H: H at position 5); 5.27 (broad s, 1H: H at position 10); 5.61 (d, J=6, 1H: H at position 2); 7.48 (t, J=7.5, 2H: OCOC$_6$H H at the meta position); 7.62 (t, J=7.5, 1H: OCOC$_6$H$_5$ H at the para position); 8.03 (d, J=7.5, 2H: OCOC$_6$H$_5$ H at the ortho position).

2α-Benzoyloxy-1β,10β-dihydroxy-7β,13α-ditriethylsilyloxy-5β,20-epoxy-4α-methoxy-9-oxo-11-taxene may be prepared in the following manner:

2.22 cm$^3$ of a 1M solution of phenyllithium in tetrahydrofuran are added at a temperature in the region of –78° C. to a solution of 940 mg of 1β,2α-carbonato-7β,13α-ditriethylsilyloxy-5β,20-epoxy-4α-methoxy-10β-methoxyacetoxy-9-oxo-11-taxene in 45 cm$^3$ of anhydrous tetrahydrofuran. The reaction mixture is stirred for 2 hours and 30 minutes at a temperature in the region of –78° C., and 20 cm$^3$ of saturated aqueous ammonium chloride solution are then added. At a temperature in the region of 20° C., 50 cm$^3$ of water and 100 cm$^3$ of ethyl acetate are added. The organic phase is separated after settling has taken place, washed with 2 times 50 cm$^3$ of saturated aqueous sodium chloride solution and then dried over magnesium sulphate. After filtration and concentration to dryness under reduced pressure (2.7 kPa) at 40° C., 1.2 mg of a product are obtained, which product is purified by chromatography on 100 g of silica (0.063–0.2 mm) contained in a column 3 cm in diameter, eluting with an ethyl acetate/cyclohexane (15:85 by volume) mixture, collecting 10 cm$^3$ fractions. Fractions containing only the desired product are pooled and concentrated to dryness under reduced pressure (2.7 kPa) at 40° C. 734 mg of 2α-benzoyloxy-1β,10β-dihydroxy-7β,13α-ditriethylsilyloxy-5β,20-epoxy-4α-methoxy-9-oxo-11-taxene are thereby obtained in the form of a white foam, the physical characteristics of which are as follows:

proton NMR spectrum (400 MHz; CDCl$_3$; δ in ppm; coupling constances J in Hz): 0.55 (mt, 6 H: ethyl CH$_2$); 0.70 (q, J=7.5, 6 H: ethyl CH$_2$); 0.93 (t, J=7.5, 9H: ethyl CH$_3$); 1.05 (t, J=7.5, 9H: ethyl CH$_3$); 1.09 (s, 3H: CH$_3$); 1.14 (s, 3H: CH$_3$); 1.55 (s, 1H: OH at position 1); 1.71 (s, 3H: CH$_3$); 2.02 and 2.33 (2 mts, 1H each: CH$_2$ at position 6); 2.07 (s, 3H: CH$_3$); 2.12 and 2.74 (2 dd, J=15 and 9 Hz and J=15 and 7.5, 1H each: CH$_2$ at position 14); 3.43 (s, 3H: OCH$_3$); 3.47 (d, J=7, 1H: H at position 3); 3.85 (dd, J=11 and 6, 1H: H7); 4.17 and 4.29 (2 d, J=8.5, 1H each: CH$_2$ 20); 4.27 (d, J=2, 1H: OH at position 10); 4.95 (mt, 1H: H at position 13); 5.00 (dd, J=10 and 3, 1H: H at position 5); 5.14 (d, J=2, 1H: H at position 10); 5.59 (d, J=7, 1H: H at position 2); 7.45 (t, J=7.5, 2H: OCOC$_6$H$_5$ H at the meta position); 7.57 (t, J=7.5, 1H: OCOC$_6$H$_5$ H at the para position); 8.07 (d, J=7.5, 2H: OCOC$_6$H$_5$ H at the ortho position).

1β,2α-Carbonato-7β,13α-bis(triethylsilyloxy)-5β,20-epoxy-4α-methoxy-10β-methoxyacetoxy-9-oxo-11-taxene may be prepared in the following manner:

0.3 g of 4 Å molecular sieves, 12 cm$^2$ of methyl iodide and 90 mg of sodium hydride are added at a temperature in the region of 20° C. and under an argon atmosphere to a solution of 510 mg of 1β,2α-carbonato-7β,13α-ditriethylsilyloxy-5β,20-epoxy-4α-hydroxy-10β-methoxyacetoxy-9-oxo-11-taxene in 6 cm$^3$ of dimethylformamide. The reaction medium is stirred at a temperature in the region of 20° C. for 3 hours. 10 cm$^3$ of saturated aqueous ammonium chloride solution and 30 cm$^3$ of dichloromethane are added. The organic phase is separated after settling has taken place, washed with 2 times 10 cm$^3$ of saturated aqueous sodium chloride solution and then dried over magnesium sulphate. After filtration and concentration to dryness under reduced pressure (2.7 kPa) at 40° C., 715 mg of a product are obtained, which product is purified by chromatography on 50 g of silica (0.063:0.2 mm) contained in a column 1 cm in diameter, eluting with an ethyl acetate/cyclohexane (25:75 by volume) mixture, collecting 10 cm$^3$ fractions. Fractions containing only the desired produced are pooled and concentrated to dryness under reduced pressure (2.7 kPa) at 40° C. 494 mg of 1β,2α-carbonato-7β,13α-ditriethylsilyloxy-5β,20-epoxy-4α-methoxy-10β-methoxyacetoxy-9-oxo-11-taxene are thereby obtained in the form of a white foam, the physical characteristics of which are as follows:

proton NMR spectrum (400 MHz; CDCl$_3$; δ in ppm; coupling constants J in Hz): 0.60 (q, J=7.5, 6H: ethyl CH$_2$); 0.68 (q, J=7.5, 6H: ethyl CH$_2$); 0.92 (t, J=7.5, 9H: ethyl CH$_3$); 1.03 (t, J=7.5, 9H: ethyl CH$_3$); 1.19 (s, 3H: CH$_3$); 1.23 (s, 3H: CH$_3$); 1.44 (s, 1H: OH at position 1); 1.71 (s, 3H: CH$_3$); 1.99 and 2.47 (2 mts, 1H each: CH$_2$ at position 6); 2.15 (s, 3H: CH$_3$); 2.32 and 2.93 (2 dd, J=15 and 9 and J=15 and 6.5, 1H each: CH$_2$ at position 14); 2.89 (d, J=5, 1H: H at position 3); 3.45 and 3.51 (2 s, 3H each: OCH$_3$); 4.10 (dd, J=10.5 and 7, 1H: H at position 7); 4.17 (limiting AB, J=16, 2H: OCOCH$_2$O); 4.41 (d, J=5, 1H: H at position 2); 4.43 and 4.79 (2 d, J=10, 1H each: CH$_2$ at position 20); 4.93 (mt, 1H: H at position 13); 5.10 (broad d, J=10, 1H: H at position 5); 6.51 (s, 1H: H at position 10).

EXAMPLE 2

15 mg of powdered 4 Å molecular sieves and 27 mg of sodium chloride are added successively to a solution of 18 mg of 2α-benzoyloxy-1β,10β-dihydroxy-5β,20-epoxy-4α-ethoxy-9-oxo-7β-trifluoromethanesulphonate-11-taxene-13α-yl (2R,3S)-3-tert-butoxycarbonylamino-2-hydroxy-3-phenylpropionate in 233 μl of acetonitrile and 23 μl of tetrahydrofuran. The reaction medium is kept stirring at a temperature in the region of 75° C. for 3 hours, and 15 cm$^3$ of dichloromethane and 15 cm$^3$ of saturated aqueous sodium chloride solution are then added at a temperature in the region of 20° C. The organic phase is separated after settling has taken place, washed with 2 times 10 cm$^3$ of saturated aqueous sodium chloride solution, then dried over magnesium sulphate, filtered and concentrated to dryness under reduced pressure (2.7 kPa) at 40° C. 22 mg of a product are obtained, which product is purified by preparative chromatography on a silica place 0.25 mm thick, eluting with a dichloromethane/methanol (95:5 by volume) mixture. 10 mg of 2α-benzoyloxy-1β,10β-dihydroxy-5β,10-epoxy-4α-ethoxy-7β,8-methylene-19-nor-9-oxo-11-taxen-13α-yl (2R,3S)-3-tert-butoxycarbonylamino-2-hydroxy-3-phenylpropionate are thereby obtained in the form of a white foam, the physical characteristics of which are as follows:

proton NMR spectrum (400 Mhz; CDCl$_3$; δ in ppm; coupling constants J in Hz): 1.21 (s, 3H: CH$_3$); 1.28 (s, 3H: CH$_3$); 1.37 (s, 9H: C(CH$_3$)$_3$); 1.35 (mt, 1H: H7); 1.47 (t, J=7, 3H: CH$_3$ of C$_2$H$_5$ at position 4); 1.72 (s, 1H: OH at position 1); 1.84 and 2.32 (t and dd, respectively, J=6 and J=10 and 6, 1H each: CH$_2$ at position 19); 1.89 (s, 3H: CH$_3$); 2.03 and 2.22 (dt and broad d, respectively, J=16 and 4 and J=16, 1H each: CH$_2$ at position 6); 2.20 and 2.90 (dd and broad dd, respectively, J=16 and 9, 1H each; CH$_2$ at position 14); 3.22 (unres.comp., 1H: OH at position 2'); 3.47 and 3.68 (2 mts, 1H each: CH$_2$ of C$_2$H$_5$ at position 4); 3.65 (d, J=7, 1H: H at position 3); 4.02 and 4.39 (2 d, J=9, 1H each: CH$_2$ at position 20); 4.26 (broad s, 1H: OH at position 10); 4.61 (mt, 1H: H at position 2'); 4.87 (mt, 1H: H at position 5); 4.95 (broad s, 1H: H at position 10); 5.33 (broad d, J=10, 1H: H at position 3'); 5.42 (d, J=10, 1H: CONH); 5.67 (d, J=7, 1H: H at position 2); 6.28 (broad t, J=9, 1H: H at position 13); from 7.30 to 7.45 (mt, 5H: aromatic H at position 3'); 7.49 (t, J=7.5, 2H: OCOC$_6$H$_5$ at the meta position); 7.60 (t, J=7.5, 1H: OCOC$_6$H$_5$ H at the para position); 8.11 (d, J=7.5, 2H: OCOC$_6$H$_5$ H at the ortho position).

2α-Benzoyloxy-1β,10β-dihydroxy-5β,20-epoxy-4α-ethoxy-9-oxo-7β-trifluoromethanesulphonyloxy-11-taxen-13α-yl (2R,3S)-3-tert-butoxycarbonylamino-2-hydroxy-3-phenylpropionate may be prepared in the following manner:

A solution of 66 mg of 2α-benzoyloxy-1β,10β-dihydroxy-5β,20-epoxy-4α-ethoxy-9-oxo-7β-trifluoromethanesulphonyloxy-11-taxene-13α-yl (2R,4S,5R)-3-tert-butoxycarbonyl-2-(4-methoxyphenyl)-4-phenyl-1,3-oxazolidine-5-carboxylate in 1.5 ml of a 0.1N solution of hydrogen chloride in ethanol is kept stirring at a temperature in the region of 0° C. for 19 hours. The reaction mixture is concentrated to dryness under reduced pressure (2.7 kPa) at 20° C. 82 mg of a product are obtained, which product is purified by preparative chromatography on a silica plate 0.25 mm thick, eluting with a dichloromethane/methanol (95:5 by volume) mixture. 20 mg of 2α-benzoyloxy-1β,10β-dihydroxy-5β,20-epoxy-4α-ethoxy-9-oxo-7β-trifluoromethanesulphonyloxy-11-taxen-13α-yl (2R,3S)-3-tert-butoxycarbonylamino-2-hydroxy-3-phenylpropionate are thereby obtained in the form of a white foam, the physical characteristics of which are as follows:

proton NMR spectrum (600 MHz; CDCl$_3$; δ in ppm coupling constants J in Hz): 1.13 (s, 3H: CH$_3$); 1.25 (s, 3H: CH$_3$); 1.40 (s, 9H: C(CH$_3$)$_3$); 1.47 (t, J=7, 3H: CH$_3$ of C$_2$H$_5$ at position 4); 1.58 (s, 1H: OH at position 1); 1.90 and 2.25 (mt and dd respectively, J=16 and 9, 1H each: CH$_2$ at position 14); 1.92 (s, 3H CH$_3$); 1.94 (s, 3H: CH$_3$); 2.40 and 2.70 (2 mts, 1H each: CH$_2$ at position 6); 3.18 (broad s, 1H: OH at position 2'); 3.43 (d, J=6.5, 1H: H at position 3); 3.75 and 3.82 (2 mts, 1H each: CH$_2$ of C$_2$H$_5$ at position 4); 4.05 (broad s, 1H: OH at position 10); 4.28 and 4.46 (2 d, J=9, 1H each: CH$_2$ at position 20); 4.63 (mt, 1H: H at position 2'); 4.92 (dd, J=11 and 7, 1H: H at position 7); 5.03 (dd, J=10 and 2, 1H: H at position 5); 5.32 (mt, 1H: H at position 3'); 5.33 (broad s, 1H: H at position 10); 5.45 (d, J=10, 1H: CONH); 5.65 (d, J=6.5, 1H: H at position 2); 6.20 (broad t, J=9, 1H: H at position 13); from 7.30 to 7.55 (mt, 5H: aromatic H at position 3'); 7.49 (t, J=7.5, 2H: OCOC$_6$H$_5$ H at the meta position); 7.61 (t, J=7.5, 1H: OCOC$_6$H$_5$ H at the para position); 8.02 (d, J=7.5, 2H: OCOC$_6$H$_5$ H at the ortho position).

2α-Benzoyloxy-1β,10β-dihydroxy-5β,20-epoxy-4α-ethoxy-9-oxo-7β-trifluoromethanesulphonate-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

60 mg of (2R,4S,5R)-3-tert-butoxycarbonyl-2-(4-methoxyphenyl)-4-phenyl-1,3-oxazolidine-5-carboxylic acid, 42 mg of dicyclohexylcarbodiimide and 5 mg of 4-(dimethylamino)pyridine are added successively at a temperature in the region of 20° C. to a solution of 90 mg of 2α-benzoyloxy-5β,20-epoxy-4α-ethoxy-9-oxo-7β-trifluoromethanesulphonyloxy-1β,10β,13α-trihydroxy-11-taxene in 4 cm$^3$ of anhydrous ethyl acetate. The reaction mixture is stirred for 6 hours under an argon atmosphere at a temperature in the region of 20° C. 30 cm$^3$ of ethyl acetate and 20 cm$^3$ of saturated aqueous ammonium chloride solution are added. The organic phase is separated after settling has taken place, washed with 2 times 20 cm$^3$ of water, then dried over magnesium sulphate, filtered and concentrated to dryness under reduced pressure (2.7 kPa) at 40° C. 140 mg of a product are obtained, which product is purified by chromatography on 30 g of silica (0.063–0.2 mm) contained in a column 1 cm in diameter, eluting with a cyclohexane/ethyl acetate (70:30 by volume) mixture collecting 8 cm$^3$ fractions. Fractions containing only the desired product are pooled and concentrated to dryness under reduced pressure (2.7 kPa) at 40° C. 110 mg of 2α-benzoyloxy-1β,10β-dihydroxy-5β,20-epoxy-4α-ethoxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white foam, the physical characteristics of which are as follows:

proton NMR spectrum (400 MHz; CDCl$_3$; δ in ppm coupling constants J in Hz): 1.10 (s, 15H: C(CH$_3$)$_3$—CH$_3$ and CH$_3$ of C$_2$H$_5$ at position 4); 1.19 (s, 3H: CH$_3$);

1.51 (s, 1H: OH at position 1); 1.64 (s, 3H: $CH_3$); 1.85 (s, 3H: $CH_3$); from 2.25 to 2.40 and 2.66 (2 mts, 1H each: $CH_2$ at position 6); from 2.25 to 2.40 and 2.88 (mt and dd respectively, J=16 and 8, 1H each: $CH_2$ at position 14); 3.35 (d, J=6.5, 1H: H at position 3); 3.52 and 3.62 (2 mts, 1H each: $CH_2$ of $C_2H_5$ at position 4); 3.84 (s, 3H: $ArOCH_3$); 4.01 (d, J=1, 1H: OH at position 10); 4.20 and 4.34 (2d, J=9, 1H each: $CH_2$ at position 20); 4.64 (d, J=4, 1H: H at position 2'); 4.85 (dd, J=11.5 and 6.5, 1H: H at position 7); 4.92 (broad d, J=10.5, 1H: H at position 5); 5.26 (d, J=1, 1H: H at position 10); 5.55 (spread unres. comp. 1H: H at position 3'); 5.59 (d, J=6.5, 1H: H at position 2); 5.91 (mt, 1H: H at position 13); 6.40 (spread unres. comp. 1H: H at position 5'); 6.94 (d, J=8.5, 2H: H at the ortho position with respect to $OCH_3$); from 7.30 to 7.50 (mt, 9H: aromatic H at position 3', H at the meta position with respect to $OCH_3$ and $OCOC_6H_5$ H at the meta position); 7.63 (t, J=7.5, 1H: $OCOC_6H_5$ H at the para position); 7.95 (d, J=7.5, 2H: $OCOC_6H_5$ H at the ortho position).

2α-Benzoyloxy-5β,20-epoxy-4α-ethoxy-9-oxo-7β-trifluoromethanesulphonyloxy-1β,10β,13α-trihydroxy-11-taxene are prepared in the following manner:

200 μl of triflic anhydride are added at a temperature in the region of 0° C. to a solution of 260 mg of 2α-benzoyloxy-5β,20-epoxy-4α-ethoxy-9-oxo-1β,7β,10β,13α-tetrahydroxy-11-taxene in 10 cm³ of dichloromethane and 145 μl of pyridine. The reaction mixture is stirred for 45 minutes at a temperature in the region of 0° C., and 15 cm³ of dichloromethane and 10 cm³ of water are then added. The organic phase is separated after settling has taken place, washed with 2 times 10 cm³ of saturated aqueous sodium hydrogen carbonate solution, then dried over magnesium sulphate, filtered and concentrated to dryness under reduced pressure (2.7 kPa) at 20° C. 308 mg of a product are obtained, which product is purified by chromatography on 60 g of silica (0.063–0.2 mm) contained in a column 1 cm in diameter, eluting with an ethyl acetate/cyclohexane (40:60 by volume) mixture and collecting 10 cm³ fractions. Fractions containing only the desired product are pooled and concentrated to dryness under reduced pressure (2.7 kPa) at 40° C. 90 mg of 2α-benzoyloxy-5β,20-epoxy-4α-ethoxy-1β,10β,13α-trihydroxy-9-oxo-7β-trifluoromethanesulphonyloxy-11-taxene are thereby obtained in the form of a white foam, the physical characteristics of which are as follows:

proton NMR spectrum (300 MHz; $CDCl_3$; δ in ppm coupling constants J in Hz): 1.07 (s, 3H: $CH_3$); 1.12 (s, 3H: $CH_3$); 1.47 (t, J=7, 3H: $CH_3$ from $C_2H_5$ at position 4); 1.87 (s, 3H: $CH_3$); 2.05 (s, 1H: OH at position 1); 2.15 (s, 3H: $CH_3$); 2.38 and 2.75 (2 mts, 1H each: $CH_2$ at position 6); 2.49 and 2.65 (2 dd, J=16 and 9 and J=16 and 3.5, respectively, 1H each: $CH_2$ at position 14); 2.89 (d, J=10, 1H: OH at position 13); 3.72 (d, J=6.5, 1H: H at position 3); from 3.80 to 3.95 (mt, 2H: $CH_2$ from $C_2H_5$ at position 4); 3.97 (d, J=1, 1H: OH at position 10); 4.30 and 4.48 (2d, J=9, 1H each: $CH_2$ at position 20); 4.57 (broad t, J=10, 1H: H at position 13); from 4.95 to 5.15 (mt, 2H: H at position 5 and H at position 7); 5.42 (d, J=1, 1H: H at position 10); 5.63 (d, J=6.5, 1H: H at position 2); 7.48 (t, J=7.5, 2H: $OCOC_6H_5$ H at the meta position); 7.63 (t, J=7.5, 1H: $OCOC_6H_5$ H at the para position); 8.00 (d, J=7.5, 2H: $OCOC_6H_5$ H at the ortho position).

2α-Benzoyloxy-5β,20-epoxy-4α-ethoxy-9-oxo-1β,7β,10β,13α-tetrahydroxy-11-taxene may be prepared in the following manner:

10 cm³ of triethylamine-hydrofluoric acid complex are added at a temperature in the region of 20° C. to a solution of 524 mg of 2α-benzoyloxy-5β,20-epoxy-4α-ethoxy-1-hydroxy-9-oxo-7β,10β,13α-tris-(triethylsilyloxy)-11-taxene in 8 cm³ of dichloromethane. The reaction mixture is stirred for 7 hours at a temperature in the region of 20° C., and 100 cm³ of dichloromethane and 200 cm³ of saturated aqueous sodium hydrogen carbonate solution are then added. The organic phase is separated after settling has taken place, washed with 2 times 50 cm³ of saturated aqueous sodium chloride solution, then dried over magnesium sulphate, filtered and concentrated to dryness under reduced pressure (2.7 kPa) at 40° C. 260 mg of 2α-benzoyloxy-5β,20-epoxy-4α-ethoxy-9-oxo-1β,7β,10β,13α-tetrahydroxy-11-taxene are thereby obtained in the form of a white foam, the physical characteristics of which are as follows:

proton NMR spectrum (400 MHz; $CDCl_3$; δ in ppm coupling constants J in Hz): 1.06 (s, 3H: $CH_3$); 1.12 (s, 3H: $CH_3$); 1.46 (t, J=7, 3H: $CH_3$ of $C_2H_5$ at position 4); 1.72 (s, 3H: $CH_3$); 1.99 and 2.50 (2 mts, 1H each: $CH_2$ at position 6); 2.04 (s, 1H: OH at position 1); 2.10 (s, 3H: $CH_3$); from 2.45 to 2.55 (mt, 1H: OH at position 7); 2.50 and 2.65 (mt and dd, respectively, J=16 and 3.5, 1H each: $CH_2$ at position 14); 3.06 (d, J=11, 1H: OH at position 13); 3.70 (d, J=6.5, 1H: H at position 3); 3.84 (mt, 1H: H at position 7); 3.89 and 3.96 (2 mts, 1H each: $CH_2$ of $C_2H_5$ at position 4); 4.15 (broad s, 1H: OH at position 10); 4.31 and 4.44 (2d, J=9 Hz, 1H each: $CH_2$ at position 20); 4.54 (broad t, J=10; 1H: H 13); 4.93 (dd, J=10 and 3.5, 1H: H at position 5); 5.28 (s, 1H: H at position 10); 5.63 (d, J=6.5, 1H: H 2); 7.48 (t, J=7.5, 2H: $OCOC_6H_5$ H at the meta position); 7.61 (t, J=7.5, 1H: $OCOC_6H_5$ H at the para position); 8.02 (d, J=7.5, 2H: $OCOC_6H_5$ H at the ortho position).

2α-Benzoyloxy-5β,20-epoxy-4α-ethoxy-1β-hydroxy-9-oxo-7β,10β,13α-tris(triethylsilyloxy)-11-taxene may be prepared according to one of the following methods:

1) 320 μl of a 1M solution of phenyllithium in tetrahydrofuran are added at a temperature in the region of –78° C. to a solution of 253 mg of 1β,2α-carbonate-5β,20-epoxy-4α-ethoxy-9-oxo-7β,10β,13α-tris(triethylsilyloxy)-11-taxene in 13 cm³ of anhydrous tetrahydrofuran. The reaction mixture is stirred for 1 hour and 30 minutes at a temperature in the region of –78° C., and 10 cm³ of saturated aqueous ammonium chloride solution are then added. At a temperature in the region of 20° C., 10 cm³ of water and 50 cm³ of ethyl acetate are added. The organic phase is separated after settling has taken place, washed with 2 times 20 cm³ of saturated aqueous sodium chloride solution, then dried over magnesium sulphate, filtered and concentrated to dryness under reduced pressure (2.7 kPa) at 40° C. 500 mg of a product are obtained, which product is purified by chromatography on 50 g of silica (0.063–0.2 mm) contained in a column 3 cm in diameter, eluting with an ethyl acetate/cyclohexane (15:85 by volume) mixture, collecting 10 cm³ fractions. Fractions containing only the desired product are pooled and concentrated to dryness under reduced pressure (2.7 kPa) at 40° C. 260 mg of 2α-benzoyloxy-5β,20-epoxy-4α-ethoxy-1β-hydroxy-9-oxo-7β,10β,13α-tris (triethylsilyloxy)-11-taxene are thereby obtained in the form of a white foam, the physical characteristics of which are as follows:

proton NMR spectrum (400 MHz; $CDCl_3$; δ in ppm coupling constants J in Hz): from 0.55 to 0.75 (mt, 18H: $CH_2$ of $C_2H_5$); from 0.90 to 1.10 (mt, 27H: $CH_3$ of $C_2H_5$); 1.15 (s, 3H: $CH_3$); 1.22 (s, 3H: $CH_3$); 1.38 (t, J=7, 3H: $CH_3$ of $C_2H_5$ in position 4); 1.50 (s, 1H: OH at position 1); 1.65 (s, 3H: CH$_3$); 2.00 and 2.39 (2 mts, 1H each: CH$_2$ at position 6); 2.02 (s, 3H CH$_3$); 2.05 and 2.85 (2 dd, J=16 and 9 and J=16 and 8.5, respectively, 1H each: CH$_2$ at position 14); 3.43 (d, J=6.5, 1H: H 3); 3.44 and 3.90 (2 mts, 1H each: CH$_2$ of C$_2$H$_5$ at position 4); 3.91 (mt, 1H: H at position 7); 4.20 and 4.30 (2d, J=9, 1H each: CH$_2$ at position 20); 4.93 (dd, J=10 and 3.5, 1H: H at position 5); 4.97 (broad t, J=9, 1H: H at position 13); 5.17 (s, 1H: H at position 10); 5.60 (d, J=6.5, 1H: H 2); 7.45 (t, J=7.5, 2H: OCOC$_6$H$_5$ H at the meta position); 7.57 (t, J=7.5, 1H: OCOC$_6$H$_5$ H at the para position); 8.06 (d, J=7.5, 2H: OCOC$_6$H$_5$ H at the ortho position).

1β,2α-Carbonato-5β,20-epoxy-4α-ethoxy-9-oxo-7β,10β, 13α-tris(triethylsilyloxy)-11-taxene may be prepared in the following manner:

0.3 of 4 Å molecular sieves, 4.2 cm$^3$ of ethyl iodide and 68 mg of 80% sodium hydride are added at a temperature in the region of 20° C. and under an argon atmosphere to a solution of 353 mg of 1β,2α-carbonato-5β,20-epoxy-4α-hydroxy-9-oxo-7β,10β,13α-tris(triethylsilyloxy)-11-taxene in 2.1 cm$^3$ of dimethylformamide. The reaction mixture is stirred at a temperature in the region of 20° C. for 1 hour. 10 cm$^3$ of saturated aqueous ammonium chloride solution and 30 cm$^3$ of dichloromethane are added. The organic phase is separated after settling has taken place, washed with 2 times 10 cm$^3$ of saturated aqueous sodium chloride solution, then dried over magnesium sulphate, filtered and concentrated to dryness under reduced pressure (2.7 kPa) at 40° C. 500 mg of a product are obtained, which product is purified by chromatography on 25 g of silica (0.063–0.2 mm) contained in a column 1 cm in diameter, eluting with an ethyl acetate/cyclohexane (10:90 by volume) mixture, collecting 10 cm$^3$ fractions. Fractions containing only the desired product are pooled and concentrated to dryness under reduced pressure (2.7 kPa) at 40° C. 253 mg of 1β,2α-carbonato-5β,20-epoxy-4α-ethoxy-9-oxo-7β,10β,13α-tris(triethylsilyloxy)-11-taxene are thereby obtained in the form of a white foam, the physical characteristics of which are as follows:

proton NMR spectrum (400 MHz; CDCl$_3$; δ in ppm coupling constants J in Hz): from 0.55 to 0.75 (mt, 18H: CH$_2$ of C$_2$H$_5$); from 0.90 to 1.10 (mt, 27H: CH$_3$ of C$_2$H$_5$); 1.17 (s, 3H: CH$_3$); 1.25 (s, 3H: CH$_3$); 1.25 (t, J=7, 3H: CH$_3$ of C$_2$H$_5$ at position 4); 1.68 (s, 3H: CH$_3$); 1.98 and 2.47 (2 mts, 1H each: CH$_2$ at position 6); 1.98 (s, 3H: CH$_3$); 2.26 and 3.07 (2 dd, J=16 and 9 and J=16 and 7, respectively, 1H each: CH$_2$ at position 14); 2.87 (d, J=5 Hz, 1H: H at position 3); 3.71 and 3.82 (2 mts, 1H each: CH$_2$ of C$_2$H$_5$ at position 4); 4.05 (dd, J=10 and 7, 1H: H at position 7); 4.39 (d, J=5, 1H: H at position 2); 4.45 and 4.77 (2d, J=9, 1H each: CH$_2$ at position 20); 4.97 (mt, 1H: H at position 13); 5.03 (broad d, J=10, 1H: H at position 5); 5.15 (6, 1H: H at position 10).

1β,2α-Carbonato-5β,20-epoxy-4α-hydroxy-9-oxo-7β, 10β,13α-tris(triethylsilyloxy)-11-taxene may be prepared in the following manner:

51 mg of imidazole and 50 μL of triethylsilane chloride are added at a temperature in the region of 20° C. and under an argon atmosphere to a solution of 98 mg of 7β,13α-bis (triethylsilyloxy)-1β,2α-carbonato-4α,10β-dihydroxy-5β, 20-epoxy-9-oxo-11-taxene in 1 cm$^3$ of dimethylformamide. The reaction mixture is stirred at a temperature in the region of 20° C. for 72 hours. 10 cm$^3$ of water and 20 cm$^3$ of ethyl acetate are added. The organic phase is separated after settling has taken place, washed with 2 times 10 cm$^3$ of saturated aqueous sodium chloride solution, then dried over magnesium sulphate, filtered and concentrated to dryness under reduced pressure (2.7 kPa) at 40° C. 190 mg of a product are obtained, which product is purified by preparative chromatography on a thin layer 2 mm thick, eluting with a cyclohexane/ethyl acetate (75:25 by volume) mixture. 58 mg of 1β,2α-carbonyldioxy-5β,20-epoxy-4α-hydroxy-9-oxo-7β,10β,13α-tris(triethylsilyloxy)-11-taxene are thereby obtained in the form of a white foam, the physical characteristics of which are as follows:

proton NMR spectrum (400 MHz; CDCl$_3$; δ in ppm coupling constants J in Hz): from 0.50 to 0.70 and 0.74 (2 mts, 12H and 6H, respectively: CH$_2$ of C$_2$H$_5$); from 0.90 to 1.10 (mt, 27H: CH$_3$ of C$_2$H$_5$); 1.14 (s, 3H: CH$_3$); 1.19 (s, 3H: CH$_3$); 1.63 (s, 3H: CH$_3$); 1.98 and 2.50 (2 mts, 1H each: CH$_2$ at position 6); 1.98 (s, 3H: CH$_3$); 2.55 and 2.67 (J=16 and 9 and J=16 and 3.5, respectively, 1H each: CH$_2$ at position 14); 3.00 (s, 1H: OH at position 4); 3.11 (d, J=5, 1H: H at position 3); 4.14 (dd, J=10 and 7, 1H: H at position 7), 4.33 (d, J=5, 1H: H 2); 4.54 (limiting AB, J=9, 2H: CH$_2$ at position 20); 4.73 (broad d, J=9, 1H: H at position 13); 4.77 (broad d, J=10, 1H: H at position 5); 5.23 (s, 1H: H at position 10).

7β,13α-Bis(triethylsilyloxy)-1β,2α-carbonato-4α,10β-dihydroxy-5β,20-epoxy-9-oxo-11-taxene may be prepared in the following manner:

0.3 g of 4 Å molecular sieves and 470 mg of zinc iodide are added at a temperature in the region of 20° C. and under an argon atmosphere to a solution of 108 mg of 7β,13α-bis (triethylsilyloxy)-1β,2α-carbonato-5β,20-epoxy-4α-hydroxy-10β-methoxyacetoxy-9-oxo-11-taxene in 3.5 cm$^3$ of methanol. The reaction mixture is stirred at a temperature in the region of 20° C. for 72 hours. 10 cm$^3$ of water and 20 cm$^3$ of ethyl acetate are added. The organic phase is separated after settling has taken place, washed with 2 times 10 cm$^3$ of saturated aqueous sodium chloride solution, then dried over magnesium sulphate, filtered and concentrated to dryness under reduced pressure (2.7 kPa) at 40° C. 90 mg of a product are obtained, which product is purified by preparative chromatography on a thin layer 2 mm thick, eluting with a cyclohexane/ethyl acetate (75:25 by volume) mixture. 56 mg of 7β,13α-bis(triethylsilyloxy)- 1β,2α-carbonato-4α, 10β-dihydroxy-5β,20-epoxy-9-oxo-11-taxene are thereby obtained in the form of a white foam, the physical characteristics of which are as follows:

proton NMR spectrum (400 Mz; CDCl$_3$,; δ in ppm; coupling constants J in Hz): 0.54 and 0.74 (2 mts, 6H each: CH$_2$ of C$_2$H$_5$); 0.91 and 1.03 (2 t, J=7.5 Hz, 9H each: CH$_3$ of C$_2$H$_5$); 1.12 (s, 3H: CH$_3$); 1.20 (s, 3H: CH$_3$); 1.72 (s, 3H: CH$_3$); 1.98 and 2.46 (2 mts, 1H each: CH$_2$ at position 6); 2.04 (s, 3H: CH$_3$); 2.55 and 2.67 (2 dd, J=16 and 9 and J=16 and 3.5, respectively, 1H each: CH$_2$ at position 14); 3.00 (s, 1H: OH at position 4); 3.14 (d, J=5, 1H: H at position 3); 4.07 (d, J=10 and 7, 1H at position 7); 4.19 (d, J=2, 1H: OH at position 10); 4.33 (d, J=5, 1H: H at position 2); 4.54 (limiting AB, J=10, 2H: CH$_2$ at position 20); 4.76 (broad d, J=9, 1H: H at position 13); 4.82 (broad d, J=10, 1H: H at position 5); 5.18 (d, J=2, 1H: H at position 10).

2) 0.3 g of 4 Å molecular sieves, 1 cm$^3$ of ethyl iodide and 34 mg of 50% sodium hydride are added at a temperature in the region of 20° C. and under an argon atmosphere to a solution of 200 mg of 2α-benzoyloxy-1β,4α-dihydroxy-5β, 20-epoxy-9-oxo-7β,10β,13α-tris(triethylsilyloxy)-11-taxene in 6 cm$^3$ of dimethylformamide. The reaction mixture is stirred at a temperature in the region of 20° C. for 1 hour. 10 cm$^3$ of saturated aqueous ammonium chloride solution and 30 cm$^3$ of ethyl acetate are added. The organic phase is separated after settling has taken place, washed with 2 times 10 cm$^3$ of saturated aqueous sodium chloride solution, then dried over magnesium sulphate, filtered and concentrated to dryness under reduced pressure (2.7 kPa) at 40° C. 320 mg are obtained, the product being purified by chromatography on 100 g of silica (0.063–0.2 mm) contained in a column 1 cm in diameter, eluting with an ethyl acetate/cyclohexane (10:90 by volume) mixture, collecting 10 cm$^3$ fractions. Fractions containing only the desired product are pooled and concentrated to dryness under reduced pressure (2.7 kPa) at 40° C. 38 mg of 2α-benzoyloxy-4α-ethoxy-5β,20-epoxy-1β-hydroxy-9-oxo-7β,10β,13α-tris(triethylsilyloxy)-11-taxene are obtained in the form of a white foam, the physical characteristics of which are identical to those of the product obtained above. 2α-Benzoyloxy-1β,4α-dihydroxy-5β,20-epoxy-9-oxo-7β,10β,13α-tris(triethylsilyloxy)-11-taxene may be prepared in the following manner:

4.6 g of imidazole and 2.35 g of triethylsilane chloride are added at a temperature in the region of 20° C. and under an argon atmosphere to a solution of 4.2 g of 2α-benzoyloxy-5β,20-epoxy-9-oxo-1β,4α,10β,13α-tetrahydroxy-7β-triethylsilyloxy-11-taxene, prepared according to D. G. Kingston et. al. Tetrahedron Letters.35, 6839 (1994), incorporated herein by reference in 50 cm$^3$ of dimethylformamide. The reaction mixture is stirred at a temperature in the region of 20° C. for 72 hours. 30 cm$^3$ of water and 100 cm$^3$ of ethyl acetate are added. The organic phase is separated after settling has taken place, washed with 2 times 30 cm$^3$ of saturated aqueous sodium chloride solution, then dried over magnesium sulphate, filtered and concentrated to dryness under reduced pressure (2.7 kPa) at 40° C. 12 g of a product are obtained, which product is purified by chromatography on 100 g of silica (0.063–0.2 mm) contained in a column 3 cm in diameter, eluting with an ethyl acetate/cyclohexane (10:90 by volume) mixture, collecting 20 cm$^3$ fractions. Fractions containing only the desired product are pooled and concentrated to dryness under reduced pressure (2.7 kPa) at 40° C. 3.6 g of 2α-benzoyloxy-1β,4α-dihydroxy-5β,20-epoxy-9-oxo-7β,10β,13α-tris(triethylsilyloxy)-11-taxene are thereby obtained in the form of a white foam, the physical characteristics of which are as follows:

proton NMR spectrum (300 MHz; CDCl$_3$; δ in ppm coupling constants J in Hz): 0.57 and from 0.60 to 0.85 (2 mts, 6H and 12H, respectively: CH$_2$ of C$_2$H$_5$); from 0.90 to 1.10 (mt, 30H: CH$_3$ of C$_2$H$_5$ and CH$_3$); 1.21 (s, 3H: CH$_3$); 1.53 (s, 3H: CH$_3$); 1.63 (s, 1H: OH at position 1); 1.96 (s, 3H: CH$_3$); 1.97 and 2.45 (2 mts, 1H each: CH$_2$ at position 6); 2.32 and 2.60 (2 dd, J=16 and 9 and J=16 and 2.5, respectively, 1H each: CH$_2$ at position 14); 3.61 (d, J=6, 1H: H at position 3); 3.80 (broad s, 1H: OH at position 4); 4.05 (dd, J=11.5 and 6, 1H: H at position 7); 4.23 and 4.27 (limiting AB, J=9, 2H: CH$_2$ at position 20); 4.64 (broad d, J=9, 1H: H at position 13); 4.71 (dd, J=10 and 4, 1H: H at position 5); 5.25 (s, 1H: H at position 10); 5.54 (d, J=6, 1H: H at position 2); 7.42 (t, J=7.5, 2H: OCOC$_6$H$_5$ H at the meta position); 7.55 (t, J=7.5, 1H: OCOC$_6$H$_5$ H at the para position); 8.11 (d, J=7.5, 2H: OCOC$_6$H$_5$ H at the ortho position).

The new products of general formula (I) in which Z represents a radical of general formula (II) manifest significant inhibitory activity with respect to abnormal cell proliferation, and possess therapeutic properties permitting the treatment of patients having pathological conditions associated with abnormal cell proliferation. The pathological conditions include the abnormal cell proliferation of malignant or non-malignant cells of various tissues and/or organs, comprising, without implied limitation, muscle, bone or connective tissue, the skin, brain, lungs, sex organs, the lymphatic or renal systems, mammary or blood cells, liver, the digestive system, pancreas and thyroid or adrenal glands. These pathological conditions can also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilms' tumour, Hodgkin's disease, melanoma, multiple myeloma, chronic lymphocytic leukaemia and acute or chronic granulocytic lymphoma. The new products according to the invention are especially useful for the treatment of cancer of the ovary. The products according to the invention may be used to prevent or delay the appearance or reappearance of the pathological conditions, or to treat these pathological conditions.

The products according to the invention may be administered to a patient according to different dosage forms suited to the chosen administration route, which is preferably the parenteral route. Parenteral administration comprises intravenous, intraperitoneal, intramuscular or subcutaneous administration. Intraperitoneal or intravenous administration is more especially preferred.

The present invention also comprises pharmaceutical compositions containing at least one product of general formula (I), in a sufficient amount suitable for use in human or veterinary therapy. The compositions may be prepared according to the customary methods, using one or more pharmaceutically acceptable adjuvants, vehicles or excipients. Suitable vehicles include diluents, sterile aqueous media and various non-toxic solvents. Preferably, the compositions take the form of aqueous solutions or suspensions, injectable solutions which can contain emulsifying agents, colourings, preservatives or stabilizers.

The choice of adjuvants or excipients may be determined by the solubility and the chemical properties of the product, the particular mode of administration and good pharmaceutical practice.

For parenteral administration, sterile, aqueous or non-aqueous solutions or suspensions are used. For the preparation of non-aqueous solutions or suspensions, natural vegetable oils such as olive oil, sesame oil or liquid petroleum, or injectable organic esters such as ethyl oleate, may be used. The sterile aqueous solutions can consist of a solution of a pharmaceutically acceptable salt dissolved in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is clearly understood that all the products participating in the compositions according to the invention must be pure and non-toxic in the amounts used.

The compositions can contain at least 0.01% of therapeutically active product. The amount of active product in a composition is such that a suitable dosage can be prescribed. Preferably, the compositions are prepared in such a way that a single dose contains from 0.01 to 1000 mg approximately of active product for parenteral administration.

The therapeutic treatment may be performed concurrently with other therapeutic treatments including antineoplastic drugs, monoclonal antibodies, immunotherapy or radiotherapy or biological response modifiers. The response modifiers include, without implied limitation, lymphokines and cytokines such as interleukins, interferons (α, β or δ) and TNF. Other chemotherapeutic agents which are useful in the treatment of disorders due to abnormal cell proliferation include, without implied limitation, alkylating agents, for instance nitrogen mustards such as mechloretamine, cyclophosphamide, melphalan and chlorambucil, alkyl sulphonates such as busulfan, nitrosoureas such as carmustine, lomustine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products, for instance vinca alkaloids such as vinblastine, vincristine and vendesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for instance cisplatin, substituted ureas such as hydroxyurea, methylhydrazine derivatives such as procarbazine, adrenocortical suppressants such as mitotane and aminoglutethymide, hormones and antagonists such as adrenocorticosteroids such as prednisone, progestins such as hydroxyprogesterone caproate, methoxyprogesterone acetate and megestrol acetate, oestrogens such as diethylstilboestrol and ethynyloestradiol, antioestrogens such as tamoxifen, and androgens such as testosterone propionate and fluoxymesterone.

The doses used for carrying out the methods according to the invention are those which permit a prophylactic treatment or a maximum therapeutic response. The doses vary according to the administration form, the particular product selected and features distinctive to the subject to be treated. In general, the doses are those which are therapeutically effective for the treatment of disorders due to abnormal cell proliferation. The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly stronger doses will be administered until an optimum effect is obtained. For other patients, it may be necessary to administer maintenance doses 1 to 8 times a day, and preferably 1 to 4 times, according to the physiological requirements of the patient in question. It is also possible that some patients may require the use of only one to two daily administrations.

In man, the doses are generally between 0.01 and 200 mg/kg. For intraperitoneal administration, the doses will generally be between 0.1 and 100 mg/kg, preferably between 0.5 and 50 mg/kg and still more specifically between 1 and 10 mg/kg. For intravenous administration, the doses are generally between 0.1 and 50 mg/kg, preferably between 0.1 and 5 mg/kg and still more specifically between 1 and 2 mg/kg. It is understood that, in order to choose the most suitable dosage, account should be taken of the administration route, the patient's weight, general state of health and age and all factors which may influence the efficacy of the treatment.

The example which follows illustrates a composition according to the invention.

EXAMPLE 40 mg of the product obtained in Example 1 are dissolved in 1 cm³ of Emulphor EL 620 and 1 cm³ of ethanol, and the solution is then diluted by adding 18 cm³ of physiological saline.

The composition is administered by infusion over 1 hour by introduction in physiological solution.

We claim:
1. A taxoid of formula I:

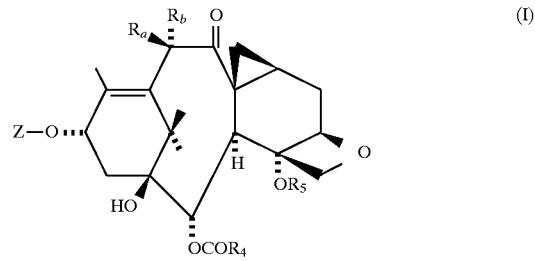

in which:

$R_a$ represents a hydrogen atom or a hydroxyl radical, an alkoxy radical containing 1 to 4 carbon atoms, an acyloxy radical containing 1 to 4 carbon atoms or an alkoxyacetoxy radical in which the alkyl portion contains 1 to 4 carbon atoms and $R_b$ represents a hydrogen atom, or alternatively $R_a$ and $R_b$, together with the carbon atom to which they are attached, form a ketone function;

Z represents a hydrogen atom or a radical of formula (II):

in which:

$R_1$ represents a benzoyl radical unsubstituted or substituted with one or more identical or different atoms or radicals selected from halogen atoms and alkyl radicals containing 1 to 4 carbon atoms, alkoxy radicals containing 1 to 4 carbon atoms or trifluoromethyl radicals, a thenoyl or furoyl radical or a radical $R_2$—O—CO— in which $R_2$ represents:

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals unsubstituted or substituted with one or more substituents selected from halogen atoms and hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals unsubstituted or substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals unsubstituted or substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl portion contains 1 to 4 carbon atoms;

a phenyl or α- or β-naphthyl radical unsubstituted or substituted with one or more atoms or radicals chosen from halogen atoms and alkyl radicals containing 1 to 4 carbon atoms or alkoxy radicals containing 1 to 4 carbon atoms, or a 5-membered aromatic heterocyclic radical;

or a saturated heterocyclic radical containing 4 to 6 carbon atoms, unsubstituted or substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical unsubstituted or substituted with one or more atoms or radicals selected from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms selected from nitrogen, oxygen and sulphur atoms and unsubstituted or substituted with one or more identical or different substituents selected from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, wherein in the substituents of the phenyl, α- or β-naphthyl and aromatic heterocyclic radicals, the alkyl radicals and the alkyl portions of the other radicals contain 1 to 4 carbon atoms, the alkenyl and alkynyl radicals contain 2 to 8 carbon atoms, and the aryl radicals are phenyl or α- or β-naphthyl radicals;

$R_4$ represents:

an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals being unsubstituted or substituted with one or more substituents selected from halogen atoms and hydroxyl radicals, alkyloxy radicals containing 1 to 4 carbon atoms, dialkylamino radicals in which each alkyl portion contains 1 to 4 carbon atoms, piperidino or morpholino radicals, 1-piperazinyl radicals unsubstituted or substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, unsubstituted or substituted phenyl radicals, cyano or carboxyl radicals or alkoxycarbonyl radicals in which the alkyl portion contains 1 to 4 carbon atoms;

or an aryl radical unsubstituted or substituted with one or more atoms or radicals selected from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro, azido, trifluoromethyl or trifluoromethoxy radicals;

or a saturated or unsaturated 4- to 6-membered heterocyclic radical unsubstituted or substituted with one or more alkyl radicals containing 1 to 4 carbon atoms; and $R^5$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals being unsubstituted or substituted with one or more substituents selected from halogen atoms and hydroxyl radicals, alkyloxy radicals containing 1 to 4 carbon atoms, dialkylamino radicals in which each alkyl portion contains 1 to 4 carbon atoms, piperidino or morpholino radicals, 1-piperazinyl radicals unsubstituted or substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, unsubstituted or substituted phenyl radicals, cyano or carboxyl radicals or alkyloxycarbonyl radicals in which the alkyl portion contains 1 to 4 carbon atoms, wherein the cycloalkyl, cycloalkenyl or bicycloalkyl radicals may be unsubstituted or substituted with one or more alkyl radicals containing 1 to 4 carbon atoms.

2. The taxoid according to claim 1 wherein:

$R_a$ represents a hydroxyl radical, an alkoxy radical containing 1 to 4 carbon atoms, an acyloxy radical containing 1 to 4 carbon atoms or an alkoxyacetoxy radical in which the alkyl portion contains 1 to 4 carbon atoms;

$R_b$ represents a hydrogen atom;

Z represents a hydrogen atom or a radical of general formula (II) in which $R_1$ represents a benzoyl radical or a radical $R_2$—O—CO— in which $R_2$ represents a tert-butyl radical;

$R_3$ represents an alkyl radical containing 1 to 6 carbon atoms, an alkenyl radical containing 2 to 6 carbon atoms, a cycloalkyl radical containing 3 to 6 carbon atoms, a phenyl radical unsubstituted or substituted with one or more identical or different atoms or radicals selected from halogen atoms and alkyl, alkoxy, dialkylamino, acylamino, alkoxycarbonylamino or trifluoromethyl radicals, or a 2- or 3-furyl, 2- or 3-thienyl or 2-, 4- or 5-thiazolyl radical;

$R_4$ represents a phenyl radical unsubstituted or substituted with one or more identical or different atoms or radicals selected from halogen atoms and alkyl, alkoxy, amino, alkylamino, dialkylamino, acylamino, alkoxycarbonylamino, azido, trifluoromethyl and trifluoromethoxy radicals, or a 2- or 3-thienyl or 2- or 3-furyl radical; and $R_5$ represents an unsubstituted or substituted alkyl radical containing 1 to 4 carbon atoms.

3. The taxoid according to claim 1 wherein:

$R_a$ represents a hydrogen atom or a hydroxyl or acetyloxy or methoxyacetoxy radical;

$R_b$ represents a hydrogen atom;

Z represents a hydrogen atom or a radical of general formula (II) in which $R_1$ represents a benzoyl radical or a radical $R_2$—O—CO— in which $R_2$ represents a tert-butyl radical;

$R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical;

$R_4$ represents a phenyl radical unsubstituted or substituted with a halogen atom; and $R_5$ represents an alkyl radical containing 1 to 4 carbon atoms.

4. A process for preparing a product according to claim 1 comprising treating a product of formula (III):

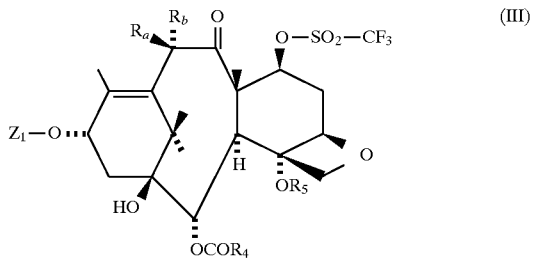

in which:

$Z_1$ represents a hydrogen atom or a radical of general formula (II) in which $R_1$ and $R_3$ are defined as in claim 1 or a radical of formula (IV):

in which:

$R_1$ and $R_3$ are defined as in claim 1;
either $R_6$ represents a hydrogen atom and $R_7$ represents a group protecting the hydroxyl function, or $R_6$ and $R_7$ together form a saturated 5- or 6-membered heterocycle;

$R_4$ and $R_5$ are defined as in claim 1;

$R_a$ represents a hydrogen atom or an alkoxy, acyloxy or alkoxyacetoxy radical or a protected hydroxyl radical, and $R_b$ represents a hydrogen atom, or alternatively $R_a$ and $R_b$, together with the nitrogen atom to which they are attached, form a ketone function;

said treating performed with an alkali metal halide or an alkali metal azide or a quaternary ammonium salt or an alkali metal phosphate to obtain a product of formula (V):

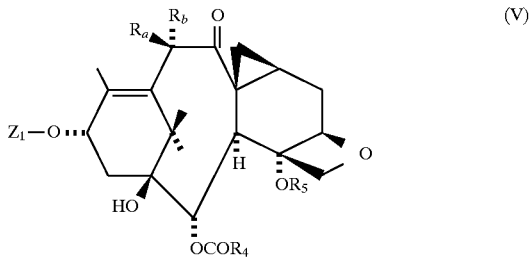

in which $Z_1$, $R_4$, $R_5$, $R_a$ and $R_b$ are defined as above, followed, if necessary, by replacement of the protective group borne by $R_a$ or of the protective groups represented by $R_7$ and/or by $R_6$ and $R_7$ by hydrogen atoms.

5. The process according to claim 4, wherein $R_4$ and $R_5$ are defined as in claim 4 and $R_a$ and $R_b$ each represent a hydrogen atom, comprising electrolytically reducing the product according to claim 1 for which $R_a$ represents a hydroxyl, acyloxy or alkoxyacetoxy radical.

6. The process according to claim 4, wherein $R_4$ and $R_5$ are defined as in claim 4 and $R_a$ and $R_b$, together with the carbon atom to which they are attached, form a ketone function, comprising oxidizing the product according to claim 1 in which $R_a$ represents a hydroxyl radical and $R_b$ represents a hydrogen atom.

7. A pharmaceutical composition, comprising at least one product of claim 1 wherein Z represents a radical of formula (II) and one or more pharmaceutically acceptable products.

8. The taxoid according to claim 1, wherein the heterocyclic radical substituent of the $R_2$ phenyl or α- or β-naphthyl radical is a fury or thienyl radical.

9. The taxoid according to claim 2, wherein the halogen atom substituent of the $R_3$ phenyl radical is fluorine, bromine, chlorine, or iodine.

10. The process according to claim 4, wherein the $R_a$ protected hydroxyl radical is a 2,2,2-trichloroethoxycarbonyloxy radical.

11. A pharmaceutical composition comprising at least one taxoid of claim 1 in which Z represents a formula (II) radical and a pharmaceutically acceptable carrier.

* * * * *

UNITED STATES PATENT AND TRADEMARK OFFICE
CERTIFICATE OF CORRECTION

PATENT NO. : 5,840,931
DATED : November 24, 1998
INVENTOR(S) : Hervé Bouchard et al.

It is certified that error appears in the above-identified patent and that said Letters Patent is hereby corrected as shown below:

On the Title Page, Item [57], in the Abstract, line 22, after "properties", insert --.--;

Claim 1, Column 28, Line 52, "unsubstituted" should read --(unsubstituted--;

Claim 1, Column 28, Line 58, "unsubstituted" should read --(unsubstituted--;

UNITED STATES PATENT AND TRADEMARK OFFICE
CERTIFICATE OF CORRECTION

PATENT NO. : 5,840,931
DATED : November 24, 1998
INVENTOR(S) : Herve Bouchard et al.

It is certified that error appears in the above-identified patent and that said Letters Patent is hereby corrected as shown below:

Claim 1, Column 29, Lines 51-52, "unsubstituted" should read --(unsubstituted--;

Claim 1, Column 30, Line 21, "unsubstituted" should read --(unsubstituted--;

Claim 8, Column 32, Line 36, "fury" should read --furyl--.

Signed and Sealed this

Twenty-seventh Day of July, 1999

Attest:

Q. TODD DICKINSON

*Attesting Officer*  *Acting Commissioner of Patents and Trademarks*